(12) United States Patent
Kovach

(10) Patent No.: US 8,058,268 B2
(45) Date of Patent: Nov. 15, 2011

(54) NEUROPROTECTIVE AGENTS FOR THE PREVENTION AND TREATMENT OF NEURODEGENERATIVE DISEASES

(75) Inventor: John S. Kovach, East Setauket, NY (US)

(73) Assignee: Lixte Biotechnology, Inc., East Setauket, NY (US)

( * ) Notice: Subject to any disclaimer, the term of this patent is extended or adjusted under 35 U.S.C. 154(b) by 155 days.

(21) Appl. No.: 12/462,182

(22) Filed: Jul. 29, 2009

(65) Prior Publication Data

US 2010/0029640 A1 Feb. 4, 2010

Related U.S. Application Data

(60) Provisional application No. 61/137,658, filed on Aug. 1, 2008.

(51) Int. Cl.
*A61K 31/54* (2006.01)
*A61K 31/44* (2006.01)

(52) U.S. Cl. .................... 514/227.8; 514/279

(58) Field of Classification Search ............... 514/227.8, 514/279
See application file for complete search history.

(56) References Cited

U.S. PATENT DOCUMENTS

| | | | |
|---|---|---|---|
| 4,143,054 A | 3/1979 | Sprague | |
| 4,218,478 A | 8/1980 | Omura et al. | |
| 4,298,752 A | 11/1981 | Dauben et al. | |
| 4,463,015 A | 7/1984 | Haslanger et al. | |
| 4,614,825 A | 9/1986 | Snitman et al. | |
| 4,654,355 A | 3/1987 | Nakane et al. | |
| 4,690,918 A | 9/1987 | Beppu et al. | |
| 4,851,423 A | 7/1989 | Girijavallabhan et al. | |
| 4,851,553 A | 7/1989 | Thottathil | |
| 5,266,710 A | 11/1993 | Patel et al. | |
| 5,326,898 A | 7/1994 | Chandraratna | |
| 5,763,647 A | 6/1998 | Ohtani et al. | |
| 5,770,382 A | 6/1998 | Hwang et al. | |
| 5,925,651 A | 7/1999 | Hutchinson | |
| 5,968,965 A | 10/1999 | Dinsmore et al. | |
| 6,222,055 B1 | 4/2001 | Wolter et al. | |
| 6,632,823 B1 | 10/2003 | Vernier et al. | |
| 6,696,483 B2 | 2/2004 | Singh | |
| 6,706,762 B1 | 3/2004 | Evans et al. | |
| 6,777,217 B1 | 8/2004 | Schreiber et al. | |
| 6,949,624 B1 | 9/2005 | Liu et al. | |
| 7,067,551 B2 | 6/2006 | Remiszewski et al. | |
| 7,154,002 B1 | 12/2006 | Bressi et al. | |
| 2002/0115826 A1 | 8/2002 | Delorme et al. | |
| 2002/0147345 A1 | 10/2002 | El Tayer et al. | |
| 2002/0177692 A1 | 11/2002 | Bartel | |
| 2003/0162186 A1 | 8/2003 | Bejanin et al. | |
| 2004/0087657 A1 | 5/2004 | Richon et al. | |
| 2004/0106141 A1 | 6/2004 | Mischel et al. | |
| 2004/0122101 A1 | 6/2004 | Miller et al. | |
| 2004/0161475 A1 | 8/2004 | Ellison et al. | |
| 2004/0197888 A1 | 10/2004 | Armour et al. | |
| 2004/0209934 A1 | 10/2004 | McCluskey et al. | |
| 2004/0253637 A1 | 12/2004 | Buechler et al. | |
| 2005/0014839 A1 | 1/2005 | Kozikowski et al. | |
| 2005/0020831 A1 | 1/2005 | Inman et al. | |
| 2005/0054626 A1 | 3/2005 | Carter et al. | |
| 2005/0136090 A1 | 6/2005 | Falotico et al. | |
| 2005/0171202 A1 | 8/2005 | Graupner et al. | |
| 2005/0203082 A1 | 9/2005 | Hsu et al. | |
| 2005/0215526 A1 | 9/2005 | Hulme et al. | |
| 2005/0222013 A1 | 10/2005 | Jung et al. | |
| 2005/0272644 A1 | 12/2005 | Chung | |
| 2005/0277583 A1 | 12/2005 | Yoshida et al. | |
| 2006/0030616 A1 | 2/2006 | McCluskey et al. | |
| 2006/0117994 A1 | 6/2006 | Ryu et al. | |
| 2006/0134682 A1 | 6/2006 | Robert et al. | |
| 2006/0167103 A1 | 7/2006 | Bacapoulos et al. | |
| 2006/0235231 A1 | 10/2006 | Joel et al. | |
| 2006/0264415 A1 | 11/2006 | Leit de Moradei et al. | |
| 2007/0004771 A1 | 1/2007 | Lee et al. | |
| 2007/0010669 A1 | 1/2007 | Breslow et al. | |
| 2007/0049576 A1 | 3/2007 | Barlow et al. | |
| 2007/0135365 A1 | 6/2007 | Tanizawa et al. | |
| 2007/0135433 A1 | 6/2007 | Dean et al. | |
| 2007/0155751 A1 | 7/2007 | Paruch et al. | |

(Continued)

FOREIGN PATENT DOCUMENTS

EP 1443967 1/2007

(Continued)

OTHER PUBLICATIONS

International Search Report in connection with PCT/US09/04378, issued Sep. 18, 2009.

(Continued)

*Primary Examiner* — Shengjun Wang
*Assistant Examiner* — Renee Claytor
(74) *Attorney, Agent, or Firm* — John P. White; Cooper & Dunham LLP

(57) ABSTRACT

Disclosed herein are methods of treating neurodegenerative diseases comprising administering to the subject a compound having the structure:

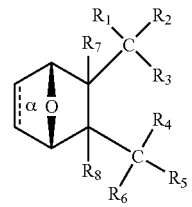

wherein α and $R_1$-$R_8$ are described herein, or a compound having the structure:

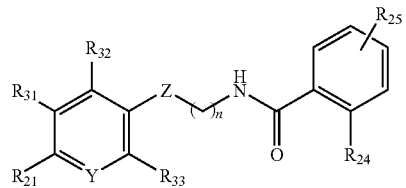

wherein Y, Z, and $R_{21}$, $R_{24}$, $R_{25}$, and $R_{31}$-$R_{33}$ are described herein.

6 Claims, 19 Drawing Sheets

U.S. PATENT DOCUMENTS

| | | | |
|---|---|---|---|
| 2007/0197550 | A1 | 8/2007 | Georgopapadakou et al. |
| 2007/0208166 | A1 | 9/2007 | Baly et al. |
| 2007/0213330 | A1 | 9/2007 | Delorme et al. |
| 2008/0132503 | A1 | 6/2008 | Moradei et al. |
| 2008/0214569 | A1 | 9/2008 | Zhuang et al. |
| 2009/0012066 | A1 | 1/2009 | Izumo et al. |
| 2009/0018142 | A9 | 1/2009 | Zhuang et al. |
| 2009/0035292 | A1 | 2/2009 | Kovach et al. |
| 2009/0036309 | A1 | 2/2009 | Kovach et al. |
| 2009/0143445 | A1 | 6/2009 | Kovach et al. |
| 2010/0029484 | A1 | 2/2010 | Kovach et al. |
| 2010/0029683 | A1 | 2/2010 | Kovach et al. |

FOREIGN PATENT DOCUMENTS

| | | |
|---|---|---|
| JP | 2007511528 | 5/2007 |
| JP | 2007514665 | 6/2007 |
| WO | WO 2005018673 | 3/2005 |
| WO | WO 2005049084 | 6/2005 |
| WO | WO 2005054257 | 6/2005 |
| WO | WO 2005058280 | 6/2005 |
| WO | WO 2005074941 | 8/2005 |
| WO | WO 2006023603 | 3/2006 |
| WO | WO 2006129105 | 12/2006 |
| WO | WO 2007014029 | 2/2007 |
| WO | WO 2007021682 | 2/2007 |
| WO | WO 2007118137 | 10/2007 |

OTHER PUBLICATIONS

Written Opinion in connection with PCT/US09/04378, issued Sep. 18, 2009.

Notification of Transmittal of the International Search Report and the Written Opinion of the International Search Authority, or the Declaration, in connection with PCT/US09/04378, issued Sep. 18, 2009.

Notification of Transmittal of the International Preliminary Report on patentability, in connection with PCT/US09/04378, issued Feb. 1, 2011.

International Preliminary Report on patentability, in connection with PCT/US09/04378, issued Feb. 1, 2011.

PCT International Application Publication WO/2007/092414, published Aug. 16, 2007.

International Search Report in connection with PCT/US2007/003095, issued Feb. 14, 2008.

International Preliminary Report on Patentability in connection with PCT/US2007/003095, issued Aug. 12, 2008.

Written Opinion in connection with PCT/US2007/003095, issued Feb. 14, 2008.

Notification of Transmittal of the International Search Report and the Written Opinion of the International Searching Authority, or the Declaration in connections with PCT/US07/03095, issued Feb. 14, 2008.

Notification Concerning Transmittal of International Preliminary Report on Patentability in connection with PCT/US07/03095, issued Aug. 21, 2008.

PCT International Application Publication No. WO 2008/097561, published Aug. 14, 2008.

Notification of Transmittal of the International Search Report and the Written Opinion of the International Searching Authority, or the Declaration in connection with PCT/US08/01549, issued May 16, 2008.

International Search Report in connection with PCT/US08/01549, issued May 16, 2008.

Written Opinion in connection with PCT/US08/01549, issued May 16, 2008.

PCT International Application Publication No. WO 2009/020565, published Feb. 12, 2009.

Notification of Transmittal of the International Search Report and the Written Opinion of the International Searching Authority, or the Declaration in connection with PCT/US08/09330, issued Nov. 4, 2008.

International Search Report in connection with PCT/US08/09330, issued Nov. 4, 2008.

Written Opinion in connection with PCT/US08/09330, issued Nov. 4, 2008.

PCT International Application Publication No. WO 2009/045440, published Apr. 9, 2009.

Notification of Transmittal of the International Search Report and the Written Opinion of the International Searching Authority, or the Declaration in connection with PCT/US08/11367, issued Dec. 12, 2008.

International Search Report in connection with PCT/US08/11367, issued Dec. 12, 2008.

Written Opinion in connection with PCT/US08/11367, issued Dec. 12, 2008.

Bastien et al. (2004) "Nuclear retinoid receptors and the transcription of retinoid-target genes." Gene vol. 328, pp. 1-16.

Blaheta, A. et al. (2002), "Valproate and Valproate-Analogues: potent Tools to Fight Against Cancer," Current Medicinal Chemistry, vol. 9 pp. 1417-1344.

Blaskovich et al. "Recent discovery and development of protein tyrosine phosphatase inhibitors." Expert Opinion on Therapeutic Patents. 2002, vol. 12, No. 6, pp. 871-905.

Camphausen et al. (2005) "Influence of in vivo growth on human glioma cell line gene expression: Convergent profiles under orthotopic conditions." Proc. Natl. Acad. Sci. USA, vol. 102, No. 23, pp. 8287-8292.

Drewinko et al. (1967), "Combination chemotherapy in vitro with adriamycin. Observations of additive, antagonistic, and synergistic effects when used in two-drug combinations on cultured human lymphoma cells," Cancer Biochem. Biophys., vol. 1, pp. 187-195.

Erdodi et al. (1995), "Endothal thioanhydride inhibits proteins phosphatases-1 and -2A inhibition, and anticancer activity," Am. J. Physol. (Cell Physiol.) vol. 38, pp. C1176-C1184.

Flicker et al. "Tyrosine kinase signaling pathways control the expression of retinoic acid receptor-a in SK-BR-3 breast cancer cells." Cancer Lett. 1997, vol. 115, pp. 63-72.

Giannini, R. and Cavallini, A. (2005), "Expression analysis of a subset of coregulators and three nuclear receptors in colorectal carcinoma." Anticancer Research, vol. 36, No. 6B, pp. 4287-4292.

Gottlicher, M et al. (2001), "Valproic acid defines a novel class of HDAC inhibitors inducing differentiation of transformed cells," EMBO Journal, vol. 20, No. 24, pp. 6969-6978.

Hart, ME et al. (2004) "Modified norcantharidine: synthesis, protein phosphatases 1 and 2A inhibition, and anticancer activity," Bioorganic & Medicinal Chemistry Letters, vol. 14, pp. 1969-1973.

Havrilesky, LJ et al. (2001), "Relationship between expression of coactivators and corepressors of hormone receptors and resistance of ovarian cancers to growth regulation by steroid hormones," J. Soc. Gynecol. Investig., vol. 8, pp. 104-113.

Hermanson et al. (2002) "N-CoR controls differentiation of neural stem cells itno astrocytes," Nature, vol. 419 pp. 934-939.

Hughes et al. (1988) "Ciliary neurotrophic factor induces type-2 astrocyte differentiation in culture." Nature, vol. 335, pp. 70-73.

Kamitami et al. (2002) "Histone acetylation may suppress human glioma cell proliferation when p21WAF/Cip1 and gelsolin are induced." Neuro-Oncology, Apr. 2002, pp. 95-101.

Kawamura, N. et al. (1990) "Endothall Thioanhydride: Structural Aspects of Unusually High Mouse toxicity and Specific Binding Site in Liver." Chem. Res. Toxicol., vol. 3, pp. 318-324.

Kelly et al. "Drug insight: histone deacetylase inhibitors-development of the new targeted anticancer agent suberoylanilide hydroxamic acid." Nature Clinical Practice Oncology, vol. 2, No. 3, pp. 150-157, Mar. 2005.

Kim et al. (2004) "Susceptibility and radiosensitization of human glioblastoma cells to Trichostatin A, a histone deacetylase inhibitor." Int. J. Radiation Oncology Biol. Phys., vol. 59, No. 4, pp. 1174-1180.

Kovach, JS, et al. (1985) "Enhancement of the antiproliferative activity of human interferon by polyamine depletion." Cancer Treat. Rep., vol. 69, pp. 97-103.

Kurebayashi et al. "Expression levels of estrogen receptor-a, estrogen receptor-b, coactivators, and corepressors in breast cancer." Clin. Cancer Res., Feb. 2000, vol. 6, pp. 512-518.

Lavinsky et al. "Diverse signaling pathways modulate nuclear receptor recruitment of N-CoR and SMRT complexes." Proc. Natl. Acad. Sci. Mar. 1998, vol. 95, pp. 2920-2925.

Mardor et al. (2001) "Monitoring Response to Convection-enhanced Taxol delivery in brain tumor patients using diffusion-weighted magnetic resonance imaging" Cancer Res., 61, pp. 4971-4973.

Matsuzawa, M. et al. (1987), "Endothal and Cantharidin Analogues: Relation of Structure to Herbicidal Activity and Mammalian Toxicity," J. Agric. Food Chem., 35 (5), pp. 823-829.

Momparlet, RL. (1980), "In vitro systems for evaluation of combination chemotherapy," Pharmacol. Ther., vol. 8, pp. 21-35.

Myers, E. et al. (2005) "Associations and Interactions Between Ets-1 and Ets-2 and Coregulatory Proteins, SRC-1, AIB1 and NCoR in Breast Cancer," Clin. Cancer Res., vol. 11, pp. 2111-2122.

Park, DM. et al. (2007) N-CoR pathway targeting induces glioblastoma derived cancer stem cell differentiation, Cell Cycle, vol. 6, issue 4, pp. 467-470.

Peng, F. et al. (2002), "Induction of apoptosis by norcantharidin in human colorectal cell lines: involvement of the CD95 receptor/ligand," J. Cancer Res. Clin. Oncol., vol. 128, pp. 223-230.

Rutka et al. (1988), "Effect of retinoids on the proliferation, morphology and expression of glial fibrillary acidic protein of an anaplastic astrocytoma cell line," Int. J. Cancer, vol. 42, pp. 419-427.

Sakoff, JA. (2004) "Protein Phosphatase Inhibition: Structure Based Design, Towards New Therapeutic Agents," Current Pharmaceutical Design, vol. 10, pp. 1139-1159.

Sanderson, L et al. (2004), "Plasma Pharmacokinetics and Metabolism of the Histone Deacetylase Inhibitor Trichostatin A after Intraperitoneal Administration to Mice," Drug Metabolism and Disposition, vol. 32, No. 10, pp. 1132-1138.

Singh et al. (2003), "Identification of a cancer stem cell in human brain tumors," Cancer Research, vol. 63, pp. 5821-5828.

Singh et al. (2004), "Identification of human brain tumour initiating cells," Nature, vol. 432, pp. 396-401.

Stupp et al. (2005) "Radiotherapy plus Concomitant and Adjuvant Temozolomide for Glioblastoma." N. Engl. J. Med., vol. 352, pp. 987-996.

Toma et al. (2005) "Retinoids and human breast cancer: in vivo effects of an antagonist for RAR-α." Cancer Lett., 219, pp. 27-31.

Touma et al. (2005) "Retinoic acid and the histone deacetylase inhibitor Trichostatin A inhibit the proliferation of human renal cell carcinoma in a xenograph tumor model." Clin. Cancer Res., 11(9), pp. 3558-2566.

Uchida et al. (2000) "Direct isolation of human central nervous system stem cells." Proc. Natl. Acad. Sci. USA, vol. 97, pp. 14720-14725.

Valeriote, F. (1975), "Synergistic interaction of anticancer agents: A cellular perspective," Cancer Chemother. Rep., vol. 59, pp. 895-900.

Wang, GS (1983), "Hydrolysis and demethylation of cantharidin on the relief of its urinary irritation," Chin. Pharmac. Bull., col. 18, pp. 18-19, with English language summary.

Wang, GS (1989), "Medical uses of mylabris in ancient China and recent studies," J. Ethnopharmacol., vol. 26, pp. 147-162.

Wang, GS et al. (1986), "Results of clinical trials in 244 cases of primary hepatoma and with norcantharidin," Chinese. Pharm. Bull., vol. 21, pp. 90-93, with English translation of abstract.

Wang, GS et al. (1987), "Effect of norcantharidin on the ' number of white blood cells," Chinese Pharm. Bull., vol. 22, pp. 517-519, with English translation of abstract.

Waters, CE et al. (2004), "Analysis of co-factor 10 function in glucocorticoid-resistant small cell carcinoma line," J. Endocrinol., vol. 183, pp. 375-383.

Weinmann et al. (2005) "Histone deacetylase inhibitors: a survey of recent patents." Expert Opin. Ther. Patents, 15(12), pp. 1677-1690.

Yoshida, M et al. (1990), "Potent and Specific Inhibition of Mammalian Histone Deacetylase Both in vivo and in vitro by Trichostatin A." Journal of Biological Chem., vol. 265, No. 28, pp. 17174-17179.

Yung et al. "Treatment of recurrent malignant gliomas with high-dose 13-cis-retinoic acid" (1996) Clin. Cancer Res. vol. 2, pp. 1931-1935.

Ayaydin, F. et al. (2000) "Inhibition of serine/threonine specific protein phosphatases causes premature activation of cdc2MsF kinase at G2/M transition and early mitotic microtubule organization in alfalfa." The Plant Journal, 23:85-96.

Baskin, T. and Wilson, J. (1997) "Inhibitors of protein kinases and phosphatases alter root morphology and disorganize cortical microtubules." Plant Physiol. 113:493-502.

Essers, M. et al., (2001) "Synthesis of the first fluorinated cantharidin analogues." Tetrahedron Lett., 42, 5429-5433.

Honkanan, R.E. et al., (1993) "Cantharidin, another natural toxin that inhibits the activity of serine/threonine protein phosphatases types 1 and 2A." FEBS Lett., 330, 283-286.

Li, Y.M. et al. (1992) "Cantharidin-binding protein: Identification as protein phosphatase 2A." Proc. Natl. Acad. Sci. USA, 89, 11867-11870.

Ramezanian, M. et al., (1989) "A new super-electrophile: alpha-(phenylsulfonyl)maleic anhydride." J. Org. Chem., 54, 2852-2854.

Berthold, F., et al. (2005) "Myeloablative megatherapy with autologous stem-cell rescue versus oral maintenance chemotherapy as consolidation treatment in patients with high-risk neuroblastoma: a randomised controlled trial." Lancet Oncol., 6:649-658.

Chang, Q., et al. (2007) "All-trans-retinoic acid induces cell growth arrest in a human medulloblastoma cell line" J. Neurooncol, 84:263-267.

Gumireddy, K., et al. (2003) "All-trans-Retinoic Acid-induced Apoptosis in Human Medulloblastoma: Activation of Caspase-3/Poly(ADPribose) Polymerase 1 Pathway." Clinical Cancer Research, 9:4052-4059.

Joshi, S., et al. (2006) "Retinoic acid receptors and tissue-transglutaminase mediate short-term effect of retinoic acid on migration and invasion of neuroblastoma SH-SY5Y cells." Oncogene, 25:240-274.

Li, X-N., et al. (2005) "Valproic acid induces growth arrest, apoptosis, and senescence in medulloblastomas by increasing histone hyperacetylation and regulating expression of p21Cip1, CDK4, and CMYC." Mol Cancer Ther., 4(12):1912-1922.

Matthay, KK., et al. (1999) "Treatment of High-Risk Neuroblastoma With Intensive Chemotherapy, Radiotherapy, Autologous Bone Marrow Transplantation, and 13-Cis-Retinoic Acid." N. Engl. J Med. ,341:1165-1173.

Abel et al. (2008) "Epigenetic targets of HDAC inhibition in neurodegenerative and psychiatric disorders", Curr. Opin. Pharmacol., 8, pp. 57-64.

Acharya et al. (2005) "Rational development of histone deacetylase inhibitors as anticancer agents: a review", Mol. Pharmacol., 68, pp. 917-932.

Adcock, I. (2007) "HDAC Inhibitors as anti-inflammatory agents" Br. J. Pharm., vol. 150, pp. 829-831.

Albert, M. S. (2007) "Changing the Trajectory of Cognitive Decline?" N. Engl. J. Med., 357(5), pp. 502-503.

Beglopoulis et al. (2006) "Regulation of CRE-dependent transcription by presenilins: prospects for therapy of Alzheimer's disease" Trends Pharmacol. Sci., 27(1), pp. 33-40.

Burke, R. E. (2007) "Inhibition of mitogen-activated protein kinase and stimulation of Akt kinase signaling pathways: Two approaches with therapeutic potential in the treatment of neurodegenerative disease" Pharmacology and Therapeutics, 114, pp. 261-277.

David et al. (1998) "Histone deacetylase associated with mSin3A mediates repression by the acute promyelocytic leukemia-associated PLZF protein" Oncogene, 16, 2549-2556.

Finnin et al (1999) "Structures of a histone deacetylase homologue bound to the TSA and SAHA inhibitors" Nature, 401, pp. 188-193.

Fischer et al. (2007) "Recovery of learning and memory is associated with chromatin remodeling" Nature, vol. 447, pp. 178-183.

Furumai et al. (2001) "Potent histone deacetylase inhibitors built from trichostatin A and cyclic tetrapeptide antibiotics including trapoxin" Proc. Natl. Acad. Sci. USA, 98(1), pp. 87-92.

Hildmann et al. (2007) "Histone deacetylases-an important class of cellular regulators with a variety of functions", Appl. Microbiol. Biotechnol., vol. 75, pp. 487-497.

Hoshikawa et al. (1994) "Trichostatin A Induces Morphological Changes and Gelsolin Expression by Inhibiting Histone Deacetylase in Human Carcinoma Cell Lines" Exp. Cell Res., 214(1), pp. 189-197.

Huang, L. (2006) "Targeting histone deacetylases for the treatment of cancer and inflammatory diseases", J. Cellular Phys., vol. 209, pp. 611-616.

Kijima et al. "Trapoxin, an Antitumor Cyclic Tetrapeptide, Is an Irreversible Inhibitor of Mammalian Histone Deacetylase" J. Biol. Chem., 268(30), pp. 22429-22435, Oct. 1993.

Kim et al. (199) "Selective Induction of Cyclin-Dependent Kinase Inhibitors and Their Roles in Cell Cycle Arrest Caused by Trichostatin A, an Inhibitor of Histone Deacetylase" Ann. N.Y. Acad. Sci., 886, pp. 200-203, Dec. 1999.

Kitamura et al. (2000) "Histone deacetylase inhibitor but not arsenic trioxide differentiates acute promyelocytic leukaemia cells with t(11,17) in combination with all-trans retinoic acid" Brit. J. Haematol., 108(4), pp. 696-702.

Korzus et al. (2004) "CBP Histone Acetyltransferase Activity Is a Critical Component of Memory Consolidation" Neuron, vol. 42, pp. 961-972.

Kozikowski et al. (2007) "Functional differences in epigenetic modulators-superiority of mercaptoacetamide-based histone deacetylase inhibitors relative to hydroxamates in cortical neuron neuroprotection studies" J. Med. Chem., 50, pp. 3054-3061.

Kwon et al. "Depudecin induces morphological reversion of transformed fibroblasts via the inhibition of histone deacetylase" Proc. Natl. Acad. Sci. USA, 95(7), pp. 3356-3361, Mar. 1998.

Langley et al. (2008) Pulse inhibition of histone deacetylases induces complete resistance to oxidative death in cortical neurons without toxicity and reveals a role for cytoplasmic p21waf1/cip1 in cell cycle-independent neuroprotection J. Neurosci., 28(1), pp. 163-176.

Levenson et al. (2004) "Regulation of Histone Acetylation during memory formation in the hippocampus" J. Biol. Chem., 29(39), pp. 40545-40559.

Lin et al (1998) "Role of the histone deacetylase complex in acute promyelocytic leukaemia" Nature, 391(6669), pp. 811-814.

Mangan et al. (2007) "Turning back the clock on neurodegeneration" Cell, vol. 129, pp. 851-853.

Mielnicki et al. (1999) "Epigenetic regulation of gelsolin expression in human breast cancer cells", Exp. Cell Res., 249(1), pp. 161-176.

Price et al. (2007) "Histone deacetylase inhibitors: an analysis of recent patenting activity" Expert Opin. Ther. Patents, 17(7), pp. 745-765.

Richon et al. "A class of hybrid polar inducers of transformed cell differentiation inhibits histone deacetylases" Proc. Natl. Acad. Sci. USA, 95(6), pp. 3003-3007, Mar. 1998.

Riester et al. (2007) "Histone deacetylase inhibitors-turning epigenic mechanisms of gene regulation into tools of therapeutic intervention in malignant and other diseases" Appl. Microbiol. Biotechnol., vol. 75, pp. 499-514.

Saito et al. "A synthetic inhibitor of histone deacetylase, MS-27-275, with marked in vivo antitumor activity against human tumors" Proc. Natl. Acad. Sci. USA, 96(8), pp. 4592-4597, Apr. 1999.

Smith, W. L., et al. (2002) "Histone deacetylase inhibitors enhance Candida albicans sensitivity to azoles and related antifungals: correlation with reduction in CDR and ERG upregulation", Antimicrob. Agents Chemother., 46(11), pp. 3532-3539.

Song et al. (2002) "Synthesis and Biological Properties of Amino Acid Amide Ligand-Based Pyridinioalkanoyl Thioesters as Anti-HIV Agents" Bioorganic and Medicinal Chem., 10(5), pp. 1263-1273.

Suzuki et al. "Synthesis and Histone Deacetylase Inhibitory Activity of New Benzamide Derivatives" J. Med. Chem., 42(15), pp. 3001-3003, 1999.

Sweatt, J. D. (2007) "Behavioural neuroscience: Down memory lane" Nature, 447, pp. 151-152.

Warrell, Jr. et al. (1998) "Therapeutic Targeting of Transcription in Acute Promyelocytic Leukemia by Use of an Inhibitor of Histone Deacetylase" J. Natl. Cancer Inst., 90, pp. 1621-1625.

Yoshida et al. (1999) "Trichostatin and Leptomycin Inhibition of Histone Deacetylation and Signal-Dependent Nuclear Export" Ann. N.Y. Acad. Sci., 886, pp. 23-35.

Science IP Search Report dated Sep. 20, 2007.

Non-final Office Action issued Mar. 30, 2009 in connection with U.S. Appl. No. 11/703,401.

McCluskey et al. (1996) "Inhibition of Protein Phosphatase 2A by Cantharidin Analogues" Bioorg. Med. Chem. Lett., 6(9), pp. 1025-1028.

McCluskey et al. (2000) "Anhydride Modified Cantharidin Analogues: Synthesis, Inhibition of Protein Phosphatases 1 and 2A and Anticancer Activity" Bioorg. Med. Chem. Lett., 10, pp. 1687-1690.

McCluskey et al. (2000) "Anhydride modified cantharidin analogues. Is ring opening important in the inhibition of protein phosphatase 2A?" Eur. J. Med. Chem., 35, pp. 957-964.

Sakoff et al. (2002) "Anticancer activity and protein phosphatase 1 and 2A inhibition of a new generation of cantharidin analogues" Invest. New Drugs, 20, pp. 1-11.

Hill et al. (2007) "Heterocyclic substituted cantharidin and norcantharidin analogues—synthesis, protein phosphatase (1 and 2A) inhibition, and anti-cancer activity" Bioorg. Med. Chem. Lett., 17, pp. 3392-3397.

Notification of Transmittal of the International Search Report and the Written Opinion of the International Search Authority, or the Declaration, in connection with PCT/US09/04108, issued Sep. 15, 2009.

International Search Report in connection with PCT/US09/04108, issued Sep. 15, 2009.

Written Opinion in connection with PCT/US09/04108, issued Sep. 15, 2009.

Notification of Transmittal of the International Search Report and the Written Opinion of the International Search Authority, or the Declaration, in connection with PCT/US09/04378, issued Sep. 18, 2009.

Levesque. Reduction of L-DOPA-induced dyskinesias by retinoid agonists: a new way to improve Parkinson's disease treatment. The Parkinson Aliance, 2004 Pilot Study Grants, abstract only.

Paez et al. "PI3K/PTEN/AKT pathway." Signal Transduction in Cancer, Kluwer Academic Publishers, 2006, vol. 115, pp. 1-28.

Sahin et al. "Retinoic Acid Isomers Protect Hippocampal Neurons From Amyloid-beta Induced Neurodegeneration." Neurotoxicity Res., 2005, vol. 7(3), pp. 243-250.

Avila et al. "Tau phosphorylation, aggregation, and cell toxicity." J. Biomedicine and Biotechnology, Hinwadi Publishing Corporation, vol. 2006, pp. 1-5.

International Search Report in connection with PCT/US09/04378, issued Sep. 18, 2009.

Written Opinion in connection with PCT/US09/04378, issued Sep. 18, 2009.

Notification of Transmittal of the International Search Report and the Written Opinion of the International Search Authority, or the Declaration, in connection with PCT/US09/04378, issued Sep. 18, 2009.

Notification of Transmittal of the International Preliminary Report on patentability, in connection with PCT/US09/04378, issued Feb. 1, 2011.

International Preliminary Report on patentability, in connection with PCT/US09/04378, issued Feb. 1, 2011.

Calcium Response to Glutamate in the Presence of Vehicle (DMSO)

Calcium Response to Glutamate in the Presence of 500nM Compound 201

Calcium Response to Glutamate in the Presence of 500nm Compound 102

NEUROPROTECTIVE AGENTS FOR THE PREVENTION AND TREATMENT OF NEURODEGENERATIVE DISEASES

This application claims the benefit of U.S. Provisional Application No. 61/137,658, filed Aug. 1, 2008, the content of of which in its entirety is hereby incorporated by reference.

Throughout this application, certain publications are referenced. Full citations for these publications may be found immediately preceding the claims. The disclosures of these publications in their entireties are hereby incorporated by reference into this application in order to describe more fully the state-of-the art to which this invention relates.

BACKGROUND OF THE INVENTION

It has been estimated that neurodegenerative diseases presently affect 20 million individuals worldwide. The cost for medical care of patients with Alzheimer's disease (AD), for example, was $91 billion in 2005 and is predicted to increase to $160 billion by 2010 (Burke 2007). Despite considerable research on the etiology and pharmacologic treatment of these diseases, no therapy is known to delay their progression (Schapira and Olanow 2004, Burke 2007). Recently, enhancing the activity of a ubiquitous regulatory protein Akt kinase has beneficial effects upon neurons of the substantia nigra of the midbrain of animals. The increased signaling of Akt mediates the improvement in the health of these neuronal cells in adult normal and aged neurons and confers almost complete protection against neurotoxin induced cell death in rodents (Ries et al, 2006).

AD and other neurodegenerative diseases are called tauopathies because they are characterized by the accumulation of aggregates of the tau protein in neurons. Tau proteins promote the assembly and stabilization of microtubular structures in neurons. The function of tau is regulated by phosphorylation at multiple serine and threonine sites (Sontag et al 1996; Tian and Wang 2002). The state of phosphorylation of tau influences its ability to bind to and enhance the polymerization of microtubules in neurons (Gong et al 2005; Meske et al 2008).

The basis by which increased Akt signaling produces neuroprotection is not certain (Burke 2007). It has been suggested that increased Akt signaling in neurons results in a decrease in the generation of deposits of neurofilaments within neurons leading to their dysfunction and eventual death (Gong et al, 2005. These filaments are composed of a structural protein called Tau. Tau proteins are susceptible to hyper-phosphorylation. Hyper-phosphorylation of tau proteins renders them inactive and results in their aggregation into paired helical filaments. These tangles of tau protein along with plaques of β-amyloid (AB) are the characteristic pathologic features of AD and the other tauopathies (Gong et al 2005).

Control of tau activity by phosphorylation is accomplished by several serine-threonine kinases, particularly glycogen synthase kinase-3β (GSK-3β). GSK-3β itself is regulated by other serine-threonine kinases especially Akt (Grimes and Jope 2001; Liu et al 2005). Activated (phosphorylated) Akt maintains GSK-3β in an inhibited (phosphorylated state). A decrease in Akt activity, that is reduced amounts of phosphorylated Akt, results in activation, that is, decreased phosphorylation of GSK-3β. Activated GSK-3β leads to hyper-phosphorylation of tau, which leads to neuronal cell death (Kaytor and Orr 2002; Baki et al 2008).

There is strong evidence from studies of human Alzheimer's disease and from a mouse model of Alzheimer's disease that failure of adequate levels of phosphorylation of GSK-3β by Akt results in hyper-phosphorylation of tau, generation of tau and amyloid plaques, and neuronal degeneration and death. In early onset familial AD (FAD) there is a defect in presenilins, trans-membrane proteins critical to normal development (Shen et al, 1997; Wong et al 1998). A member of this family, presenilin-1 (PS1), regulates PI3K/Akt signaling (Sherrington et al 1995; Baki et al 2004; Kang et al 2005; Uemura et al 2007). In primary neuronal cultures of cells from PS1 −/− mice, Baki et al (2008) showed that there was inadequate PI3K-Akt signaling resulting in decreased phosphorylation of GSK-3β, hyper-phosphorylation of tau, and progressive neurodegeneration. The addition of normal presenilin-1 or of PI3K-Akt increased GSK-3β phosphorylation and suppressed neuronal cell death.

Ries et al. (2006) showed that increasing the concentration of activated Akt inhibits cell death of dopamine neurons of the substantia nigra in mouse model of Parkinson's disease induced by 6-hydroxy dopamine. Increasing Akt activity in the brain of normal adult and also aged mice enhanced the integrity and function of existing dopamine neurons (Ries et al., 2006). In a mouse model of AD, animals with genetically engineered increased amounts of GSK-3β in the forebrain have all the histologic and, to the extent that they can be assessed in the mouse, functional defects of human AD. Elimination of over-expression of GSK-3β by suppression of the transgene results in a return toward normal of all histologic and functional signs of AD (Engel et al 2006).

Neurodegenerative diseases such as AD are frequently characterized by impaired learning and memory. The mechanism(s) responsible for these most troublesome symptoms are associated with death of neuronal cells. At a molecular level, the basis for changes in memory formation and consolidation has been linked to the activity of histone deacetylases chromatin structures (Korzus et al, 2004; Levenson et al, 2004). Beglopoulos and Shen (2006) found that inhibitors of phosphodiesterase 4 and histone deacetylases reduce memory deficits and neurodegeneration in animal models of AD affecting cAMP response element (CRE) genes. Recently, Fischer et al (2007) reported improved learning behavior and access to long-term memories after significant neuronal loss and brain atrophy can be reestablished in a mouse model by environmental enrichment and by treatment with inhibitors of histone deacetylases (see reviews and commentaries by Sweat, 2007; Mangan and Levenson 2007; Albert 2007; Abel and Zukin; 2008).

Acetylation and deacetylation have a critical role in regulation of gene expression, cellular proliferation, development and differentiation, with aberrant deacetylation leading to a multitude of disorders (Abel and Zukin, 2008). Histone deacetylase inhibitors (HDACi) have anti-inflammatory and neuroprotective effects in models of stroke and Alzheimer's disease (AD) (Abel and Zukin, 2008). Inhibitors of protein phosphatase 2A (PP2Ai), primarily the shellfish toxin, okadaic acid, have neuroprotective effects in some model systems but are injurious in others (Tian and Wang, 2002).

Thus, there is substantial evidence that AD is a pathologic condition resulting from inadequate activity of the enzyme Akt and excessive activity of GSK-3β and that reduction of GSK-3β activity may reduce the severity of precipitated tau proteins, with a lessening of neurological deficit. In addition, there appears to be a poorly understood component of neurodegenerative diseases related to excessive histone deacetylase activity, or at least a condition of reduced acetylation of certain histones that is corrected by increased acetylation resulting in improved learning and memory. Non-toxic drugs that protect and foster the survival of acute and chronically diseased neurons are urgently needed.

The compounds described herein reduce the activity of GSK-3β and increase the acetylation of neuronal histones.

SUMMARY OF THE INVENTION

This invention disclosed herein provides a method of treating a subject with a neurodegenerative disease comprising administering to the subject a compound having the structure

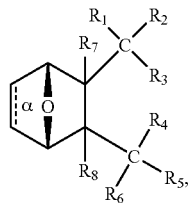

wherein bond α is present or absent; $R_1$ and $R_2$ is each independently H, $O^-$ or $OR_9$, where $R_9$ is H, alkyl, alkenyl, alkynyl or aryl, or $R_1$ and $R_2$ together are =O; $R_3$ and $R_4$ are each different, and each is OH, $O^-$, $OR_9$, SH, $S^-$, $SR_9$,

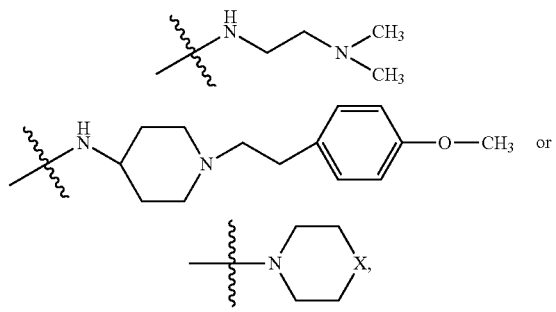

where X is O, S, $NR_{10}$, or $N^+R_{10}R_{10}$, where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O,

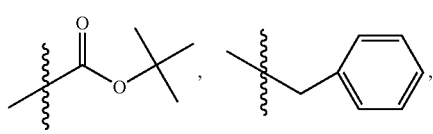

—$CH_2CN$, —$CH_2CO_2R_{11}$, —$CH_2COR_{11}$, —$NHR_{11}$ or —$NH^+(R_{11})_2$, where each $R_{11}$ is independently alkyl, alkenyl or alkynyl, each of which is substituted or unsubstituted, or H; $R_5$ and $R_6$ is each independently H, OH, or $R_5$ and $R_6$ taken together are =O; and $R_7$ and $R_8$ is each independently H, F, Cl, Br, $SO_2Ph$, $CO_2CH_3$, or $SR_{12}$, where $R_{12}$ is H, aryl or a substituted or unsubstituted alkyl, alkenyl or alkynyl, or a salt, enantiomer or zwitterion of the compound, or a compound having the structure

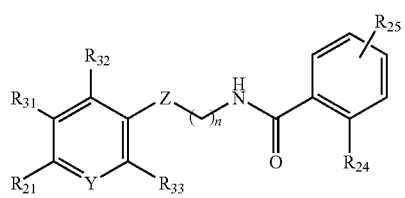

wherein n is 1-10; Y is C—$R_{30}$ or N, wherein $R_{30}$ is H, OH, SH, F, Cl, $SO_2R_{26}$, $NO_2$, trifluoromethyl, methoxy, or CO—$R_{26}$, wherein $R_{26}$ is alkyl, alkenyl, alkynyl, $C_3$-$C_8$ cycloalkyl, or aryl; Z is

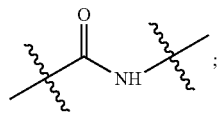

$R_{21}$ is H or $NR_{22}R_{23}$, wherein $R_{22}$ and $R_{23}$ are each independently H, $C_1$-$C_6$ alkyl, or $C_3$-$C_8$ cycloalkyl; $R_{24}$ is OH or SH; and $R_{25}$, $R_{31}$, $R_{32}$, and $R_{33}$ are each independently H, OH, SH, F, Cl, $SO_2R_{34}$, $NO_2$, trifluoromethyl, methoxy, or CO—$R_{34}$, wherein $R_{34}$ is alkyl, alkenyl, alkynyl, $C_3$-$C_8$ cycloalkyl, or aryl, or a salt of the compound, in an amount effective to treat the subject.

This invention also provides a method for reducing the amount of GSK-3β in a neural cell comprising contacting the cell with an effective amount of a compound having the structure

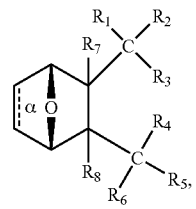

wherein bond α is present or absent; $R_1$ and $R_2$ is each independently H, $O^-$ or $OR_9$, where $R_9$ is H, alkyl, alkenyl, alkynyl or aryl, or $R_1$ and $R_2$ together are =O; $R_3$ and $R_4$ are each different, and each is OH, $O^-$, $OR_9$, SH, $S^-$, $SR_9$,

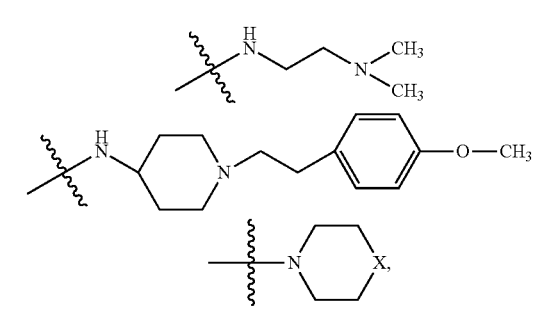

where X is O, S, $NR_{10}$, or $N^+R_{10}R_{10}$, where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O,

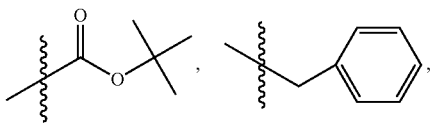

—CH$_2$CN, —CH$_2$CO$_2$R$_{11}$, —CH$_2$COR$_{11}$, —NHR$_{11}$ or —NH$^+$(R$_{11}$)$_2$, where each R$_{11}$ is independently alkyl, alkenyl or alkynyl, each of which is substituted or unsubstituted, or H; R$_5$ and R$_6$ is each independently H, OH, or R$_5$ and R$_6$ taken together are =O; and R$_7$ and R$_8$ is each independently H, F, Cl, Br, SO$_2$Ph, CO$_2$CH$_3$, or SR$_{12}$, where R$_{12}$ is H, aryl or a substituted or unsubstituted alkyl, alkenyl or alkynyl, or a salt, enantiomer or zwitterion of the compound, or a compound having the structure

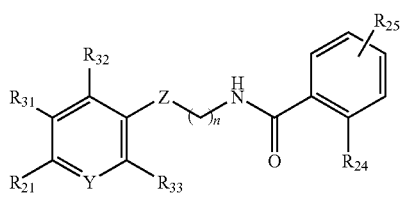

wherein n is 1-10; Y is C—R$_{30}$ or N, wherein R$_{30}$ is H, OH, SH, F, Cl, SO$_2$R$_{26}$, NO$_2$, trifluoromethyl, methoxy, or CO—R$_{26}$, wherein R$_{26}$ is alkyl, alkenyl, alkynyl, C$_3$-C$_8$ cycloalkyl, or aryl; Z is

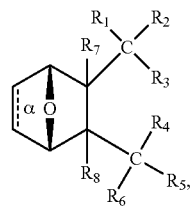

R$_{21}$ is H or NR$_{22}$R$_{23}$, wherein R$_{22}$ and R$_{23}$ are each independently H, C$_1$-C$_6$ alkyl, or C$_3$-C$_8$ cycloalkyl; R$_{24}$ is OH or SH; and R$_{25}$, R$_{31}$, R$_{32}$, and R$_{33}$ are each independently H, OH, SH, F, Cl, SO$_2$R$_{34}$, NO$_2$, trifluoromethyl, methoxy, or CO—R$_{34}$, wherein R$_{34}$ is alkyl, alkenyl, alkynyl, C$_3$-C$_8$ cycloalkyl, or aryl, or a salt of the compound, so as to thereby reduce the amount of GSK-3β in the neural cell.

Also provided is a method for increasing the amount of phosphorylated Akt in a neural cell comprising contacting the neural cell with an effective amount of a compound having the structure

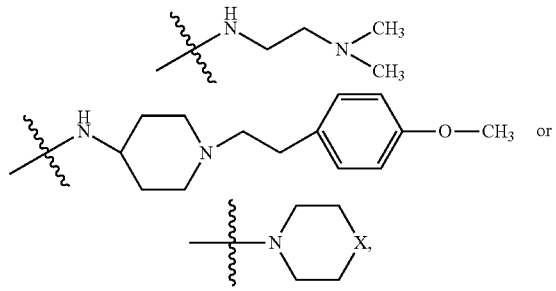

wherein bond α is present or absent; R$_1$ and R$_2$ is each independently H, O$^-$ or OR$_9$, where R$_9$ is H, alkyl, alkenyl, alkynyl or aryl, or R$_1$ and R$_2$ together are =O; R$_3$ and R$_4$ are each different, and each is OH, O$^-$, OR$_9$, SH, S$^-$, SR$_9$, where X is O, S, NR$_{10}$, or N$^+$R$_{10}$R$_{10}$ where each R$_{10}$ is independently H, alkyl, substituted C$_2$-C$_{12}$ alkyl, alkenyl, substituted C$_4$-C$_{12}$ alkenyl, alkynyl, substituted alkynyl, aryl, substituted aryl where the substituent is other than chloro when R$_1$ and R$_2$ are =O,

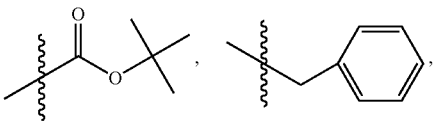

—CH$_2$CN, —CH$_2$CO$_2$R$_{11}$, —CH$_2$COR$_{11}$, —NHR$_{11}$ or —NH$^+$(R$_{11}$)$_2$, where each R$_{11}$ is independently alkyl, alkenyl or alkynyl, each of which is substituted or unsubstituted, or H; R$_5$ and R$_6$ is each independently H, OH, or R$_5$ and R$_6$ taken together are =O; and R$_7$ and R$_8$ is each independently H, F, Cl, Br, SO$_2$Ph, CO$_2$CH$_3$, or SR$_{12}$, where R$_{12}$ is H, aryl or a substituted or unsubstituted alkyl, alkenyl or alkynyl, or a salt, enantiomer or zwitterion of the compound, or a compound having the structure

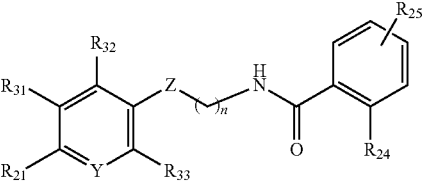

wherein n is 1-10; Y is C—R$_{30}$ or N, wherein R$_{30}$ is H, OH, SH, F, Cl, SO$_2$R$_{26}$, NO$_2$, trifluoromethyl, methoxy, or CO—R$_{26}$, wherein R$_{26}$ is alkyl, alkenyl, alkynyl, C$_3$-C$_8$ cycloalkyl, or aryl; Z is

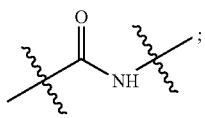

R$_{21}$ is H or NR$_{22}$R$_{23}$, wherein R$_{22}$ and R$_{23}$ are each independently H, C$_1$-C$_6$ alkyl, or C$_3$-C$_8$ cycloalkyl; R$_{24}$ is OH or SH; and R$_{25}$, R$_{31}$, R$_{32}$, and R$_{33}$ are each independently H, OH, SH, F, Cl, SO$_2$R$_{34}$, NO$_2$, trifluoromethyl, methoxy, or CO—R$_{34}$, wherein R$_{34}$ is alkyl, alkenyl, alkynyl, C$_3$-C$_8$ cycloalkyl, or aryl, or a salt of the compound, so as to thereby increase the amount of phosphorylated Akt in the neural cell.

This invention further provides a method for reducing the phosphorylation of tau in a neural cell, comprising contacting the neural cell with an effective amount of a compound having the structure

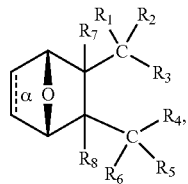

wherein bond α is present or absent; $R_1$ and $R_2$ is each independently H, O⁻ or $OR_9$, where $R_9$ is H, alkyl, alkenyl, alkynyl or aryl, or $R_1$ and $R_2$ together are =O; $R_3$ and $R_4$ are each different, and each is OH, O⁻, $OR_9$, SH, S⁻, $SR_9$,

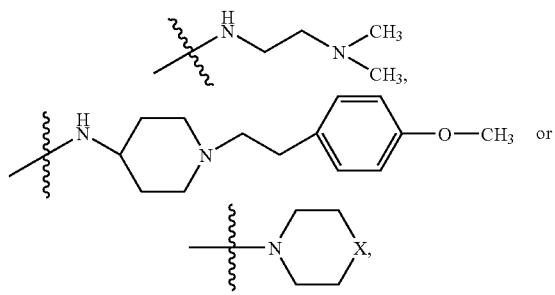

where X is O, S, $NR_{10}$, or $N^+R_{10}R_{10}$, where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O,

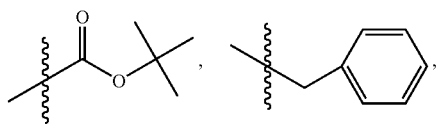

—$CH_2CN$, —$CH_2CO_2R_{11}$, —$CH_2COR_{11}$, —$NHR_{11}$ or —$NH^+(R_{11})_2$, where each $R_{11}$ is independently alkyl, alkenyl or alkynyl, each of which is substituted or unsubstituted, or H; $R_5$ and $R_6$ is each independently H, OH, or $R_5$ and $R_6$ taken together are =O; and $R_7$ and $R_8$ is each independently H, F, Cl, Br, $SO_2Ph$, $CO_2CH_3$, or $SR_{12}$, where $R_{12}$ is H, aryl or a substituted or unsubstituted alkyl, alkenyl or alkynyl, or a salt, enantiomer or zwitterion of the compound, or a compound having the structure

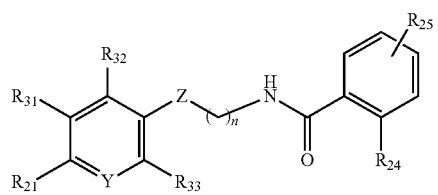

wherein n is 1-10; Y is C—$R_{30}$ or N, wherein $R_{30}$ is H, OH, SH, F, Cl, $SO_2R_{26}$, $NO_2$, trifluoromethyl, methoxy, or CO—$R_{26}$, wherein $R_{26}$ is alkyl, alkenyl, alkynyl, $C_3$-$C_8$ cycloalkyl, or aryl; Z is

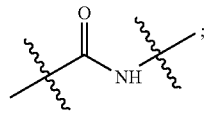

$R_{21}$ is H or $NR_{22}R_{23}$, wherein $R_{22}$ and $R_{23}$ are each independently H, $C_1$-$C_6$ alkyl, or $C_3$-$C_8$ cycloalkyl; $R_{24}$ is OH or SH; and $R_{25}$, $R_{31}$, $R_{32}$, and $R_{33}$ are each independently H, OH, SH, F, Cl, $SO_2R_{34}$, $NO_2$, trifluoromethyl, methoxy, or CO—$R_{34}$, wherein $R_{34}$ is alkyl, alkenyl, alkynyl, $C_3$-$C_8$ cycloalkyl, or aryl, or a salt of the compound, so as to thereby reduce the phosphorylation of tau in the neural cell.

The medulloblastoma cells, DAOY, in culture were exposed to Compound 100, Compound 205 or vehicle alone. After 4 hours western blots were made for p-Akt, total Akt, and beta actin. Control cells (C) showed only trace amounts of p-Akt and substantial amounts of total Akt and beta actin. Exposure to Compound 205, a compound with no anti-PP2A activity, had no effect. Exposure to Compound 100 revealed induction of p-Akt and an increase in total Akt relative to beta actin.

Figure 1:
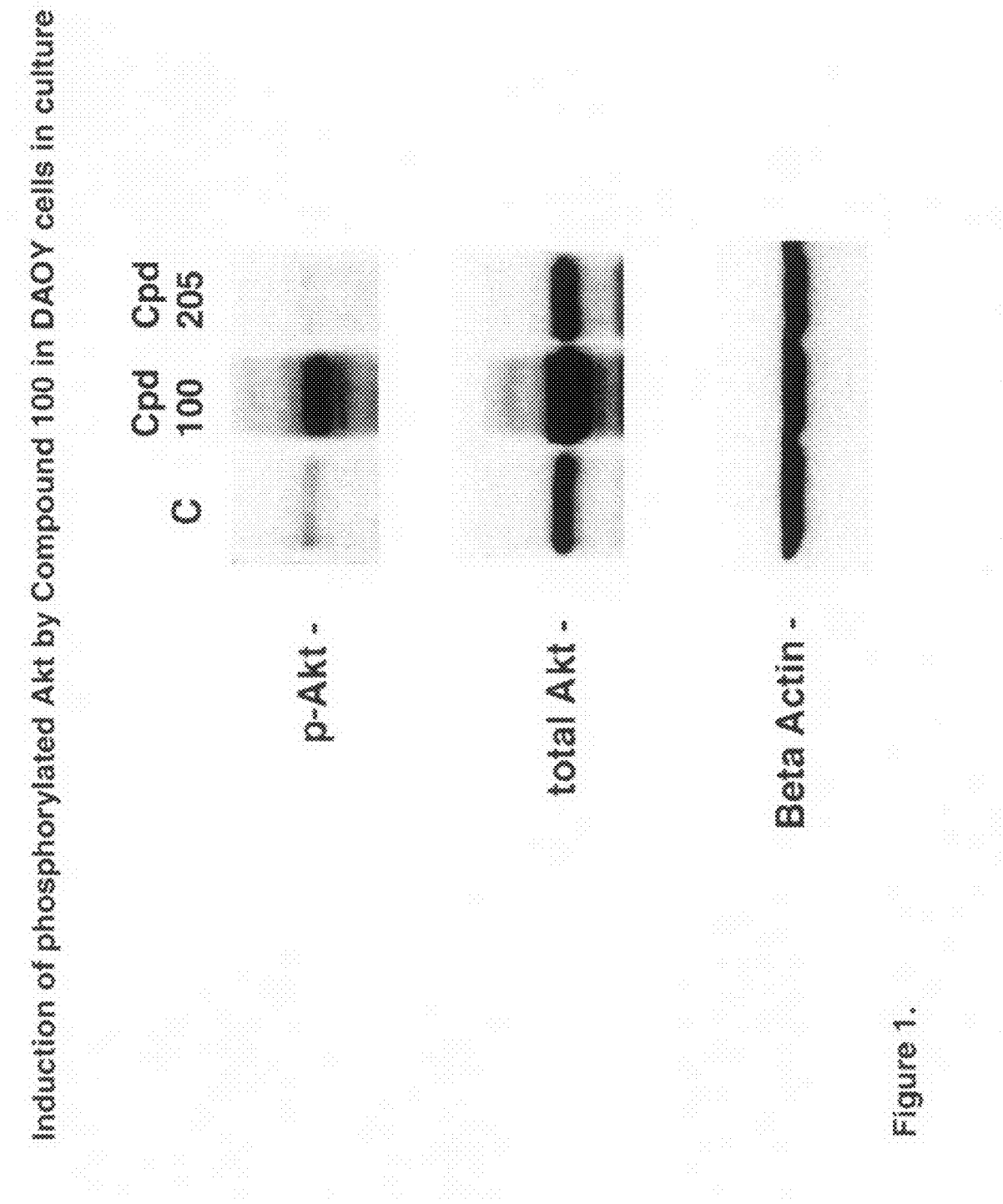
FIG. 1: Induction of phosphorylated Akt by Compound 100 in DAOY cells in culture.
Figure 2:
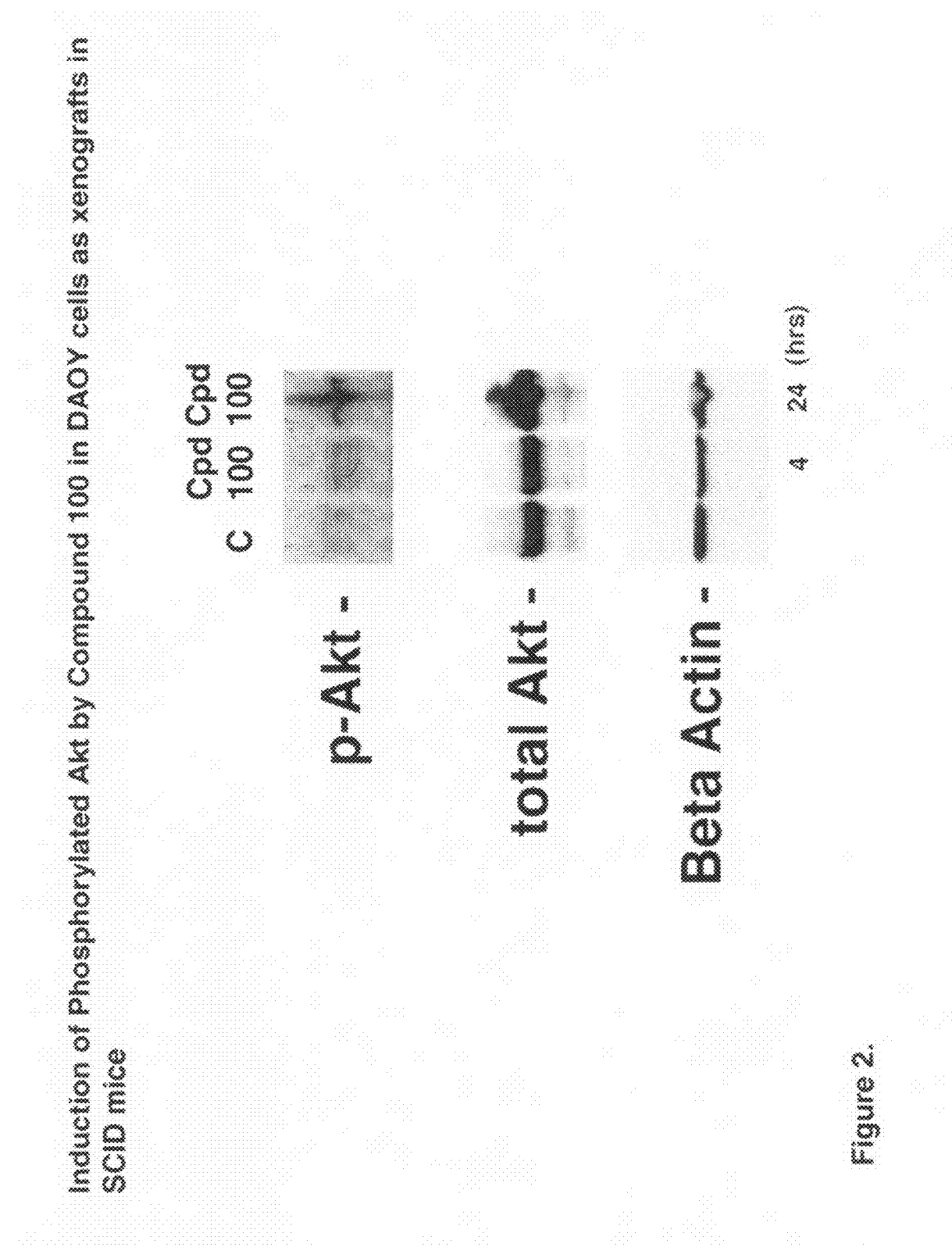

FIG. 2: Induction of phosphorylated Akt by Compound 100 in DAOY cells growing as xenografts in SCID mice.

SCID mice with human medulloblastoma cells, DAOY, implanted subcutaneously were treated with 0.03 mg/20 gram mouse with Compound 100 or vehicle alone. After 4 hours and 24 hours western blots were made for p-Akt, total Akt, and beta actin. Control cells (C) at both time points (only 24 hour point shown) had only trace amounts of p-Akt and substantial amounts of total Akt and beta actin. Exposure to Compound 100 revealed induction of p-Akt and an increase in total Akt relative to beta actin.

Figure 3:
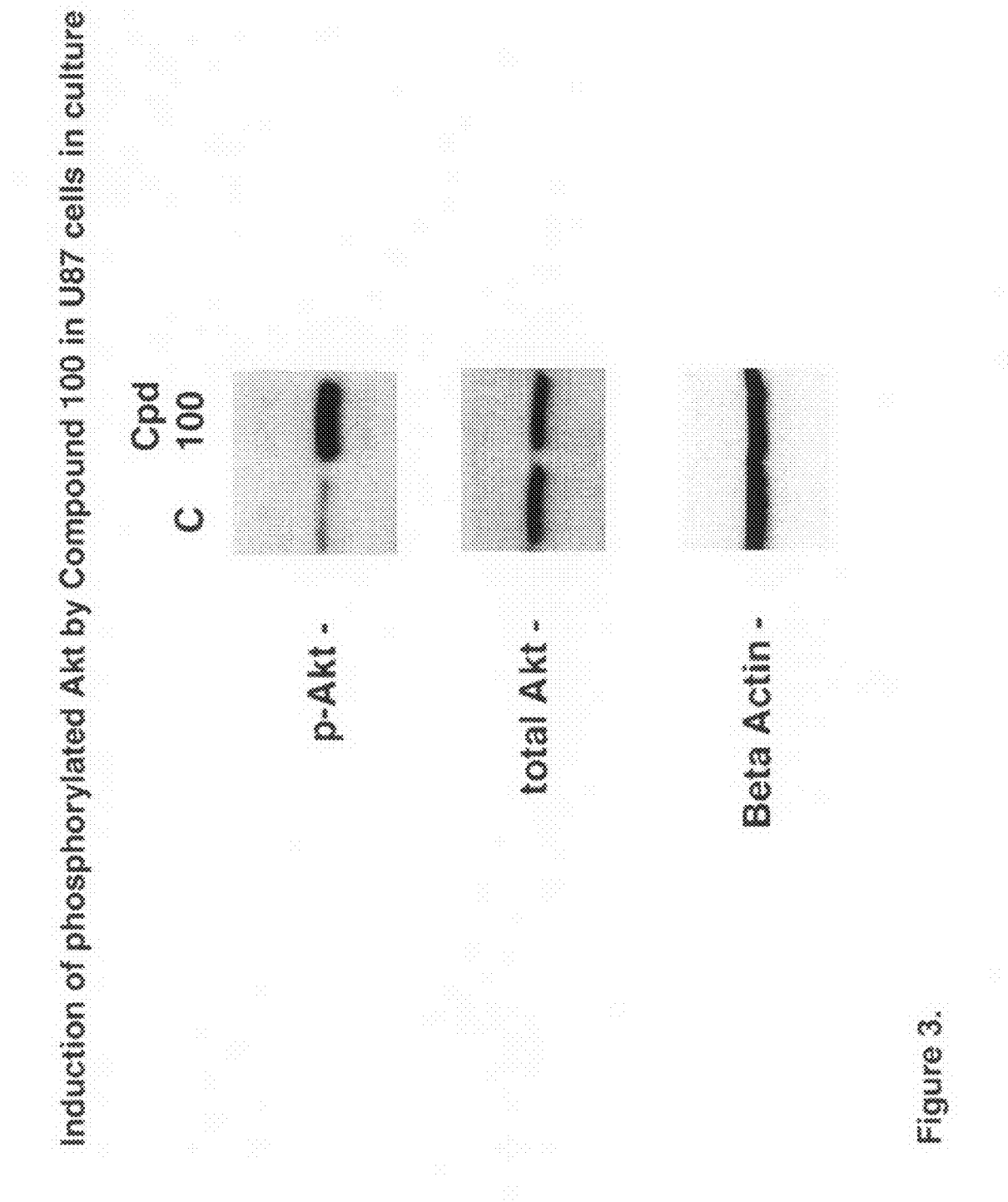

FIG. 3: Induction of phosphorylated Akt by Compound-100 in U87 cells in culture.

The human glioblastoma cells, U87, were exposed to compound 100 or vehicle alone. After 4 hours western blots were made for p-Akt, total Akt, and beta actin. Control cells (C) showed only trace amounts of p-Akt and substantial amounts of total Akt and beta actin. Exposure to Compound 100 revealed induction of p-Akt and an increase in total Akt relative to beta actin.

Figure 4:
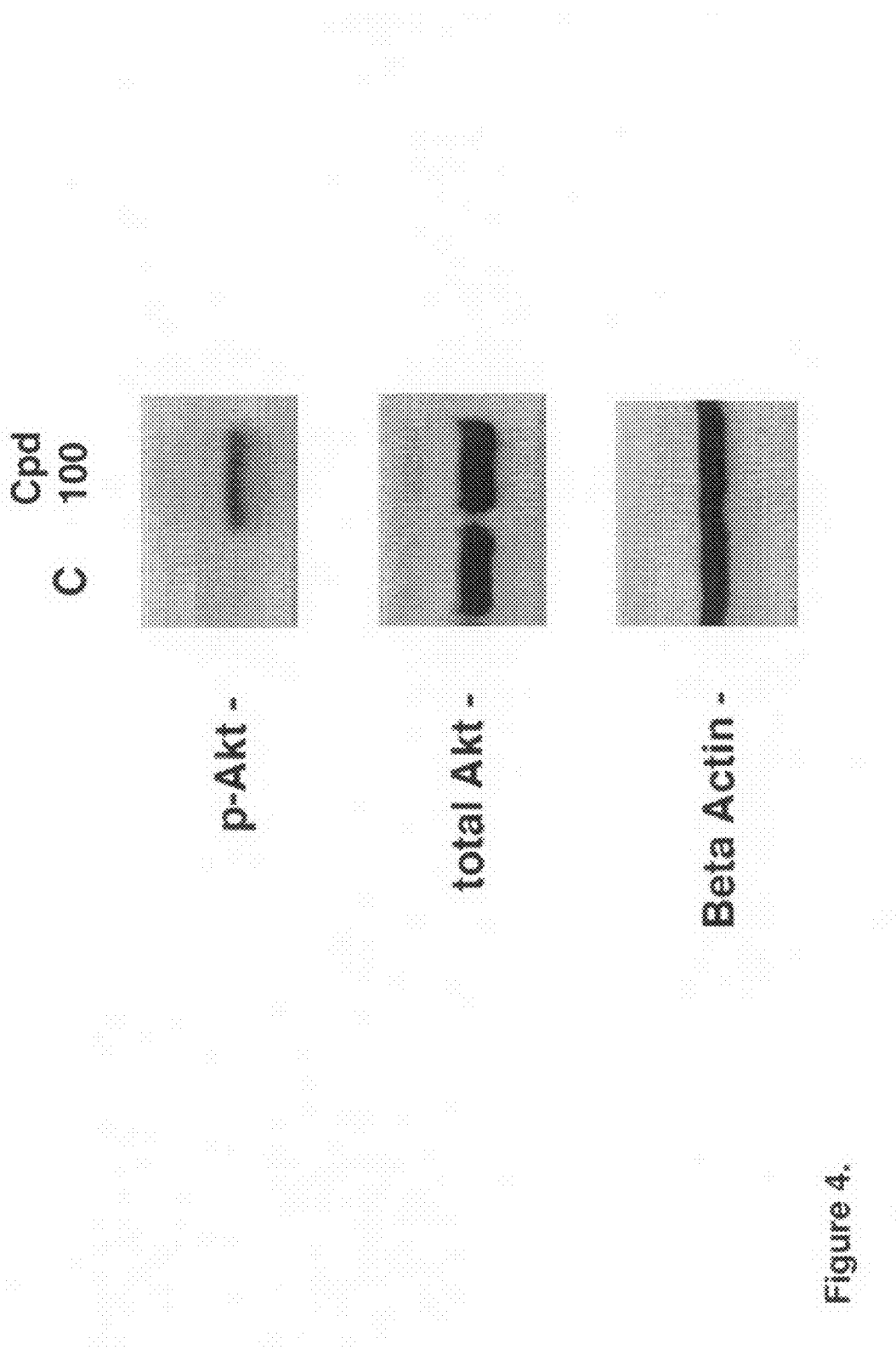

FIG. 4: Induction of phosphorylated Akt by Compound-100 in U87 cells growing as xenografts in SCID mice.

SCID mice with human glioblastoma cells, U87, implanted subcutaneously were treated with 0.03 mg/20 gram mouse with Compound 100 or vehicle alone. After 4 hours, western blots were made for p-Akt, total Akt, and beta actin. Control cells (C) showed only trace amounts of p-Akt and substantial amounts of total Akt and beta actin. Exposure to Compound 100 revealed induction of p-Akt and an increase in total Akt relative to beta actin.

Figure 5:
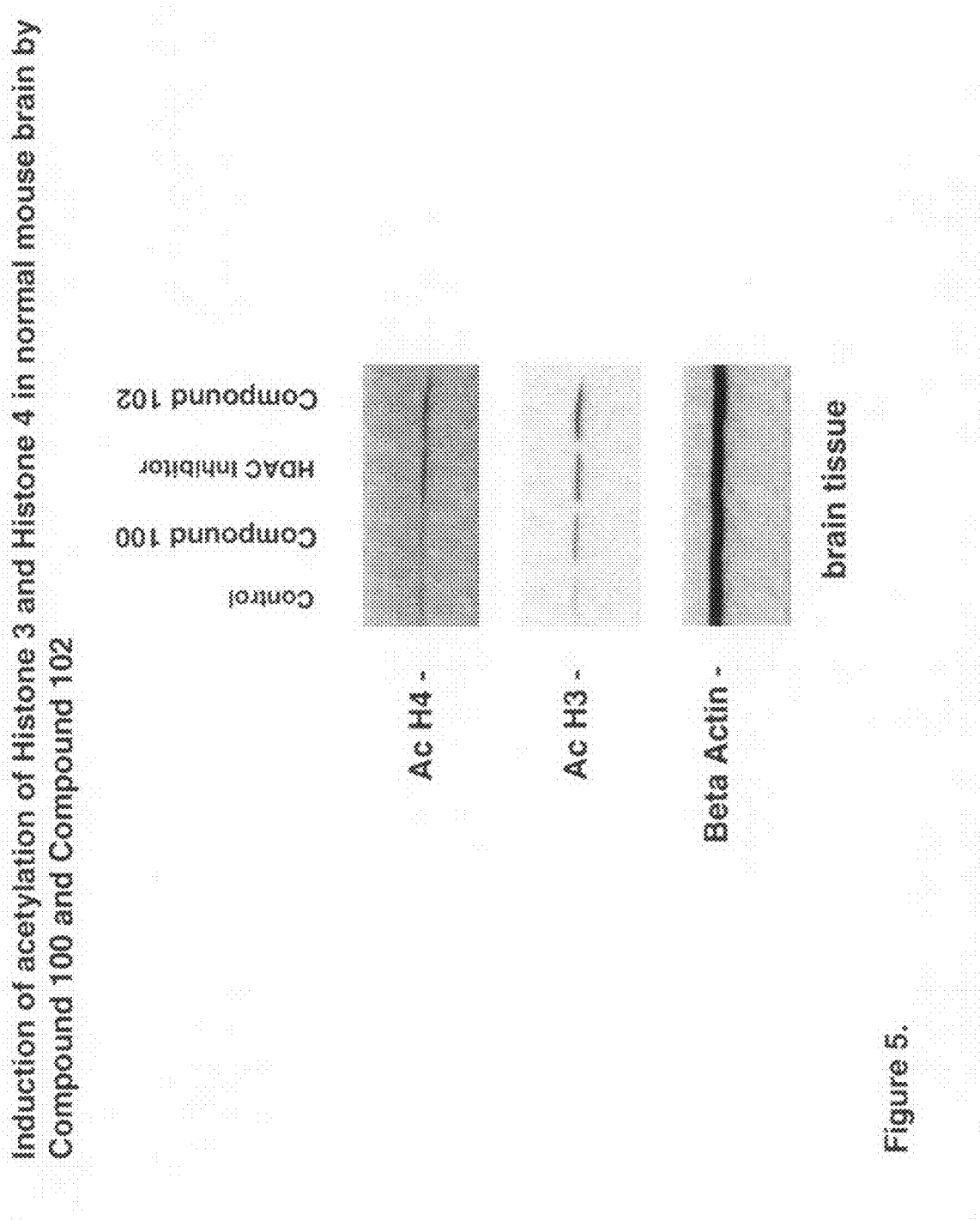

FIG. 5: Induction of acetylation of Histone 3 and Histone 4 in normal mouse brain by Compound 100 and Compound 102.

Normal mice were treated with Compound 100 and Compound 102, 0.03 mg/20 gram mouse. After 4 hours of exposure, treated and control animals (vehicle alone) animals were sacrificed and western blots for acetylated histone 3 and histone 4 were made. Both drugs increased acetylation of the histones compared to control tissue.

Figure 6:
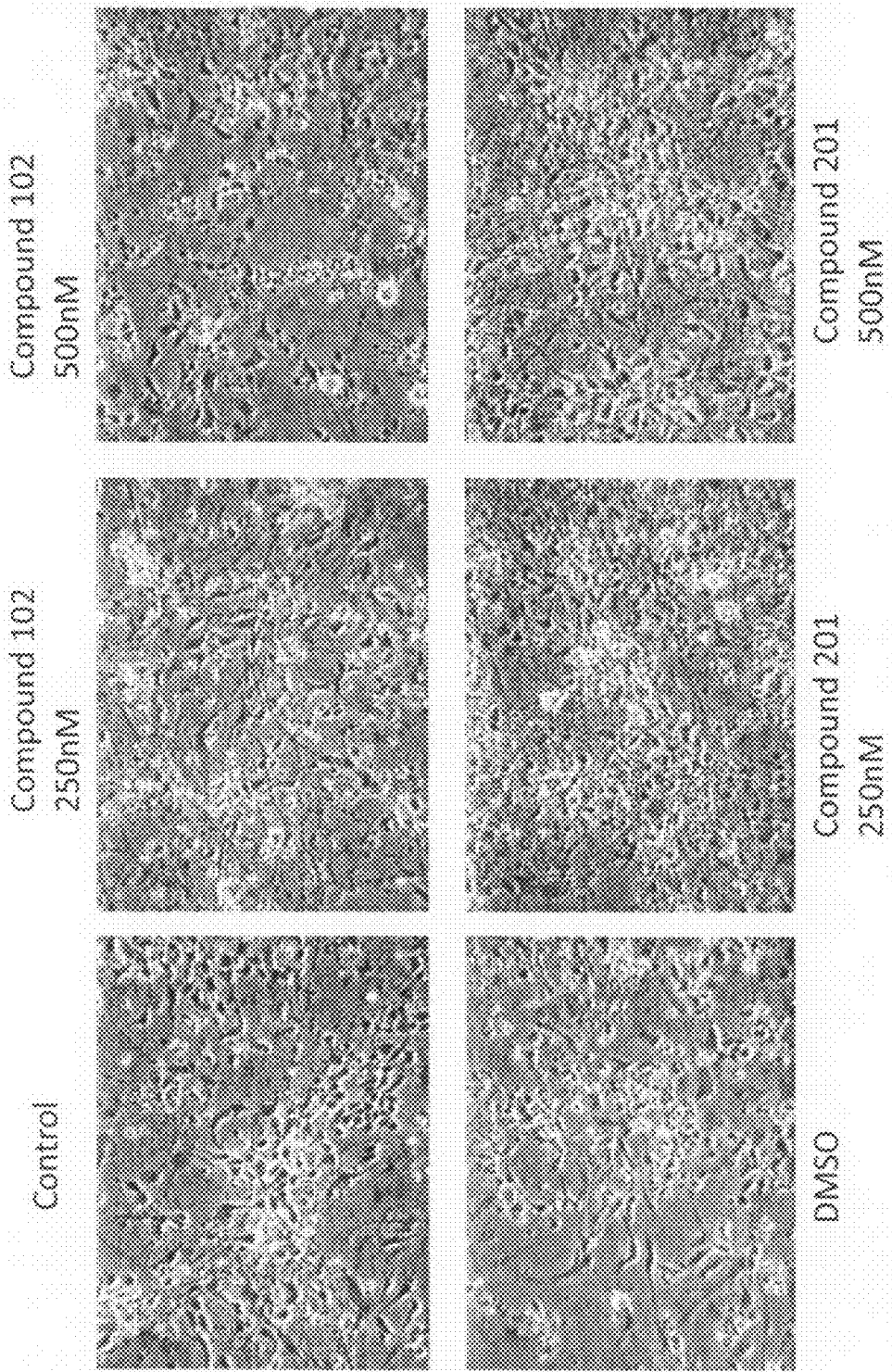

FIG. 6. Photomicrographs of primary embryonal rat cortical neuronal cells at 23 days subjected to environmental stress by exposure to growth factor deficient medium for 1 hour on day 3 of culture.

Figure 7:
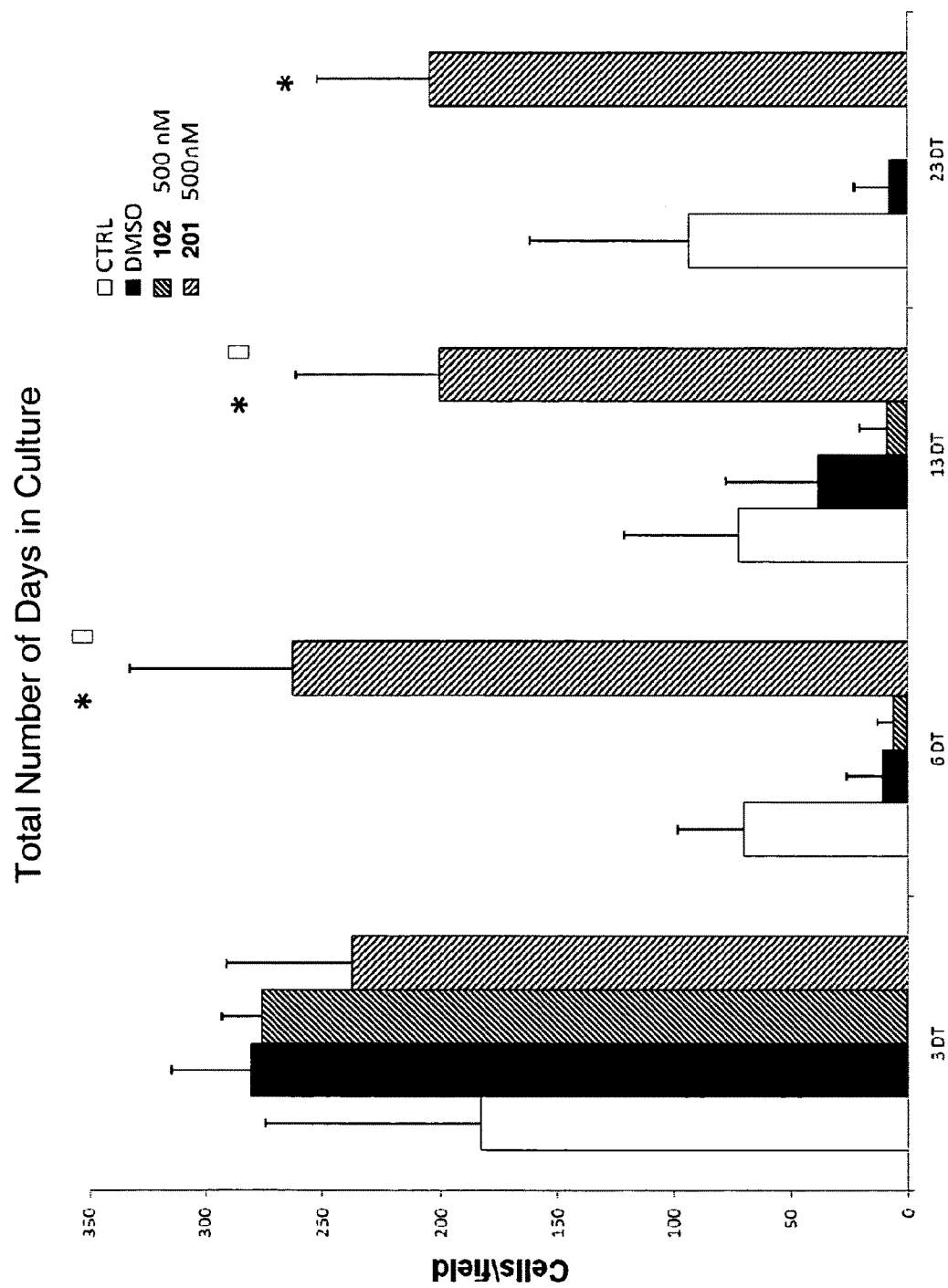

FIG. 7. Average number of primary embryonal rat cortical neuronal cells at 3, 6, 13, and 23 days in culture (n=4).

All cultures were exposed to growth factor deficient medium for 1 hour on day 3 followed by of culture in complete medium containing no supplement (control), drug vehicle (0.05% DMSO), compound 102 (500 nM), or compound 201 (500 nM). Only exposure to compound 201 resulted in statistically significant ($p \leq 0.01$) protection of cell integrity.

Figure 8:
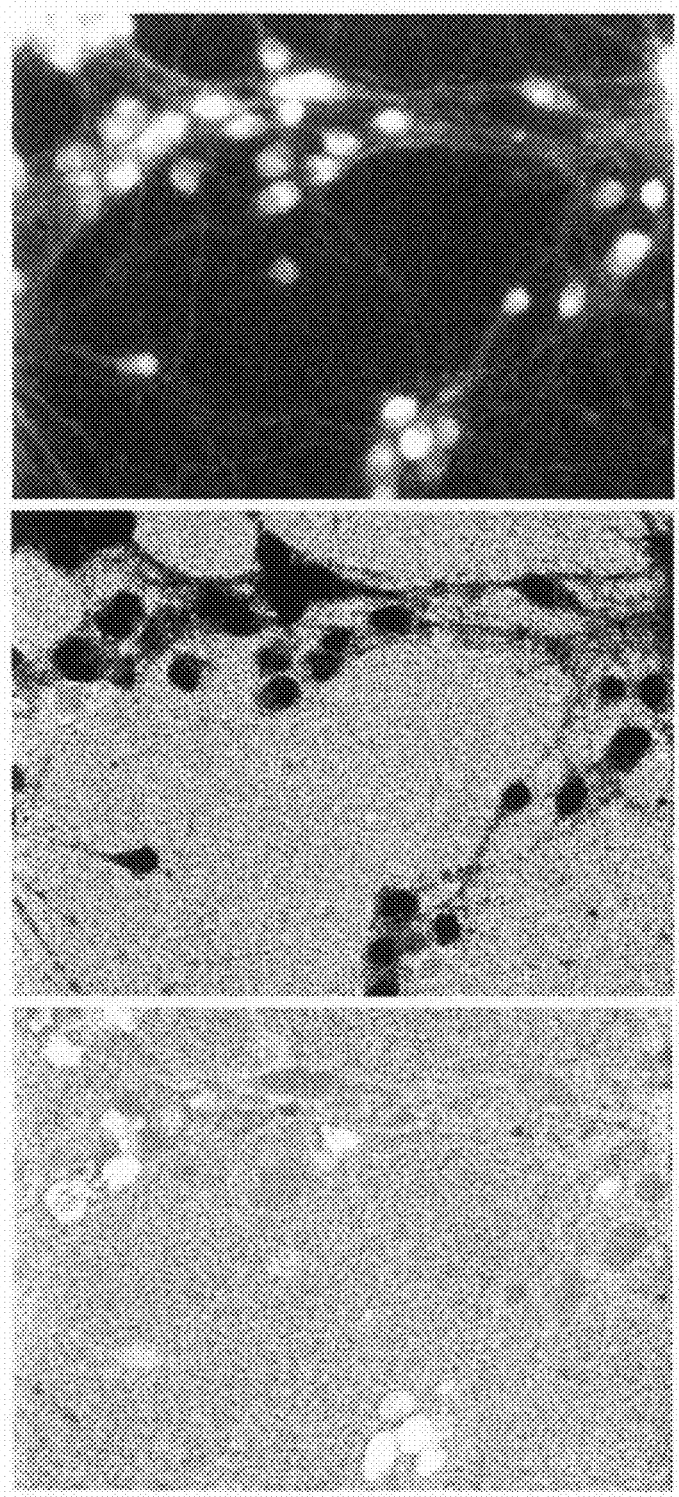
Figure 9:
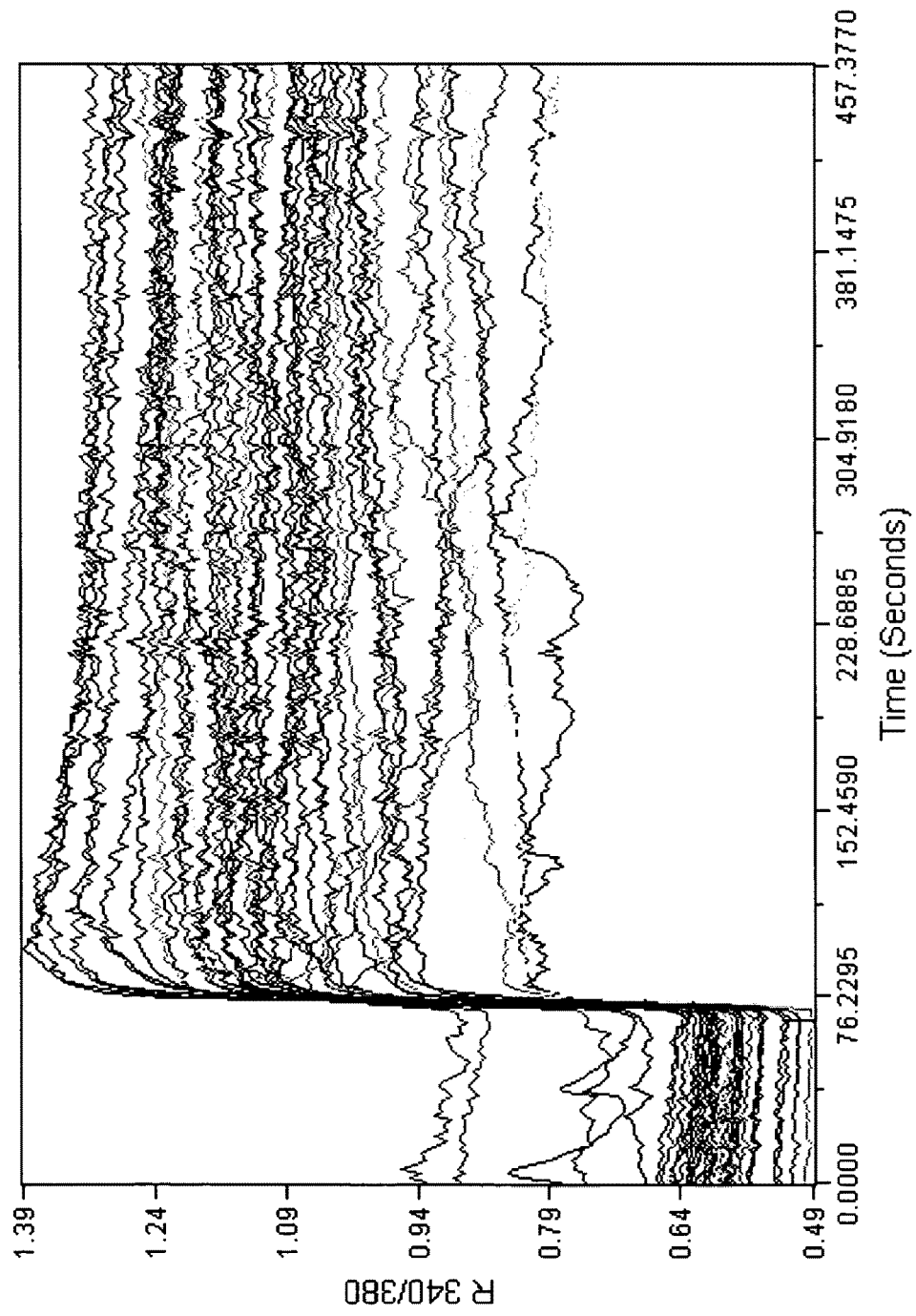
Figure 10:
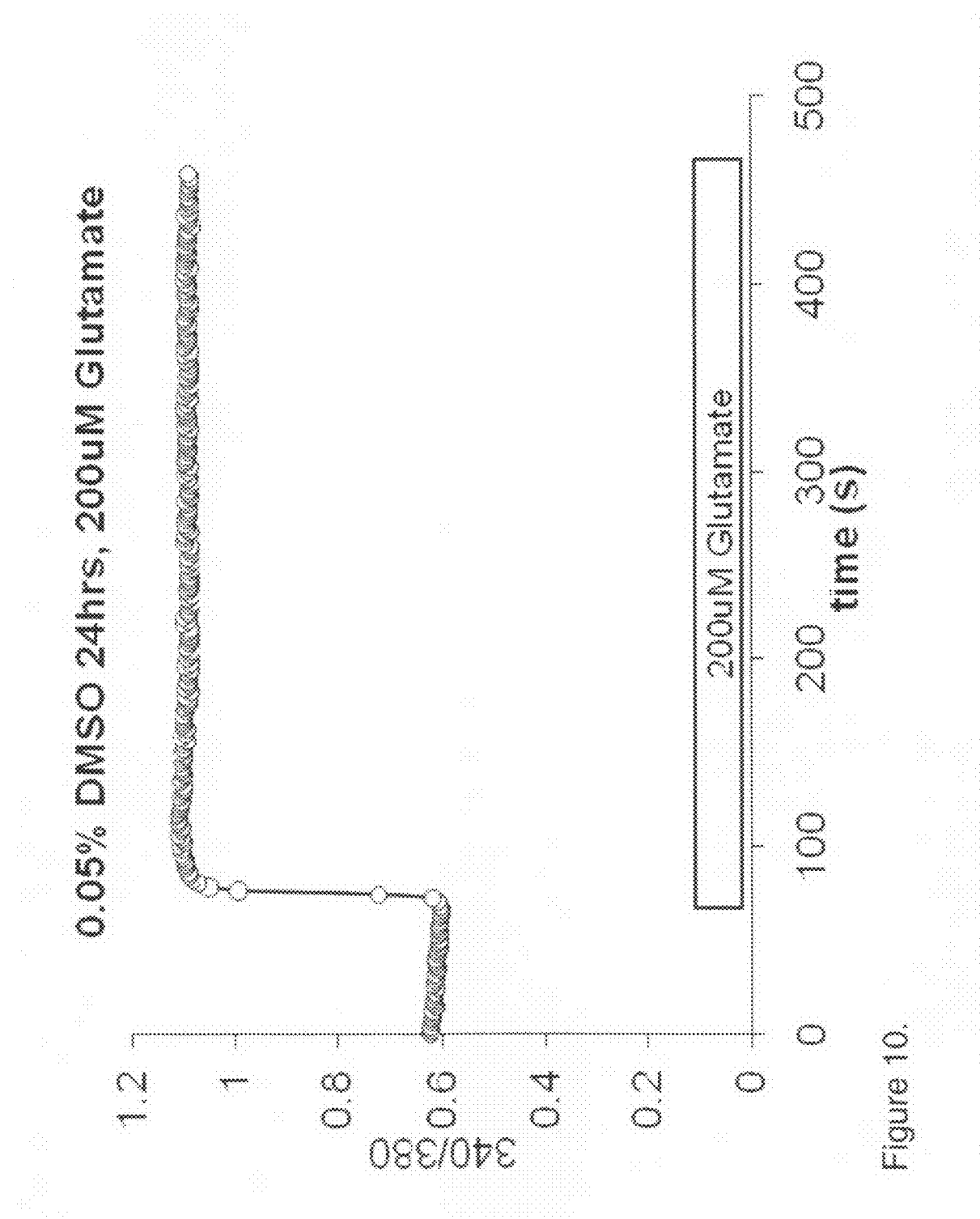

FIGS. 8-10. Calcium response to acute exposure of 200 uM glutamate in the presence of vehicle (0.05% DMSO).

FIG. 8 shows photomicrographs of one field of cells in which change in calcium flux was measured in individual cells (FIG. 9), and then averaged (FIG. 10).

FIGS. 11-14. Calcium response to acute exposure to 200 uM glutamate in the presence of 500 nm Compound 102.

Figure 11:
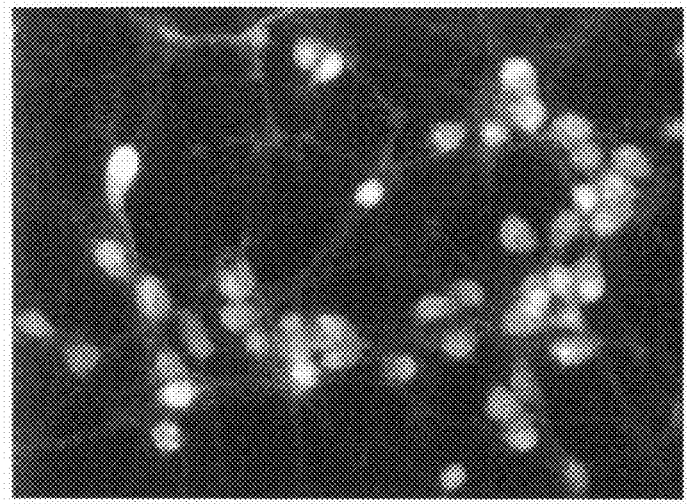
Figure 11:
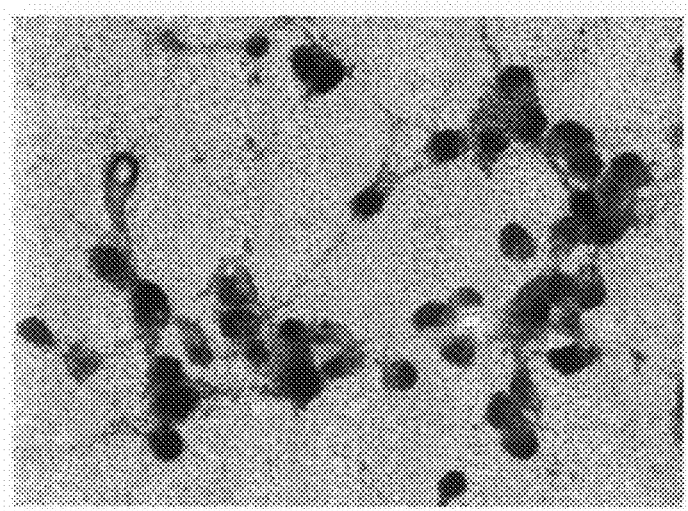
Figure 11:
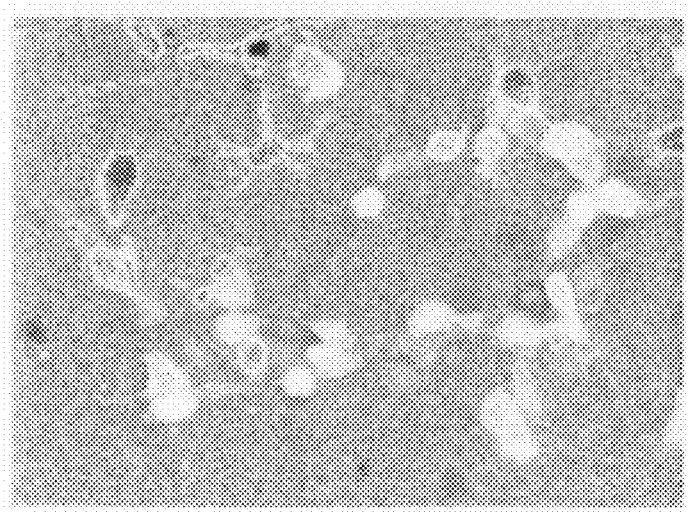
Figure 12:
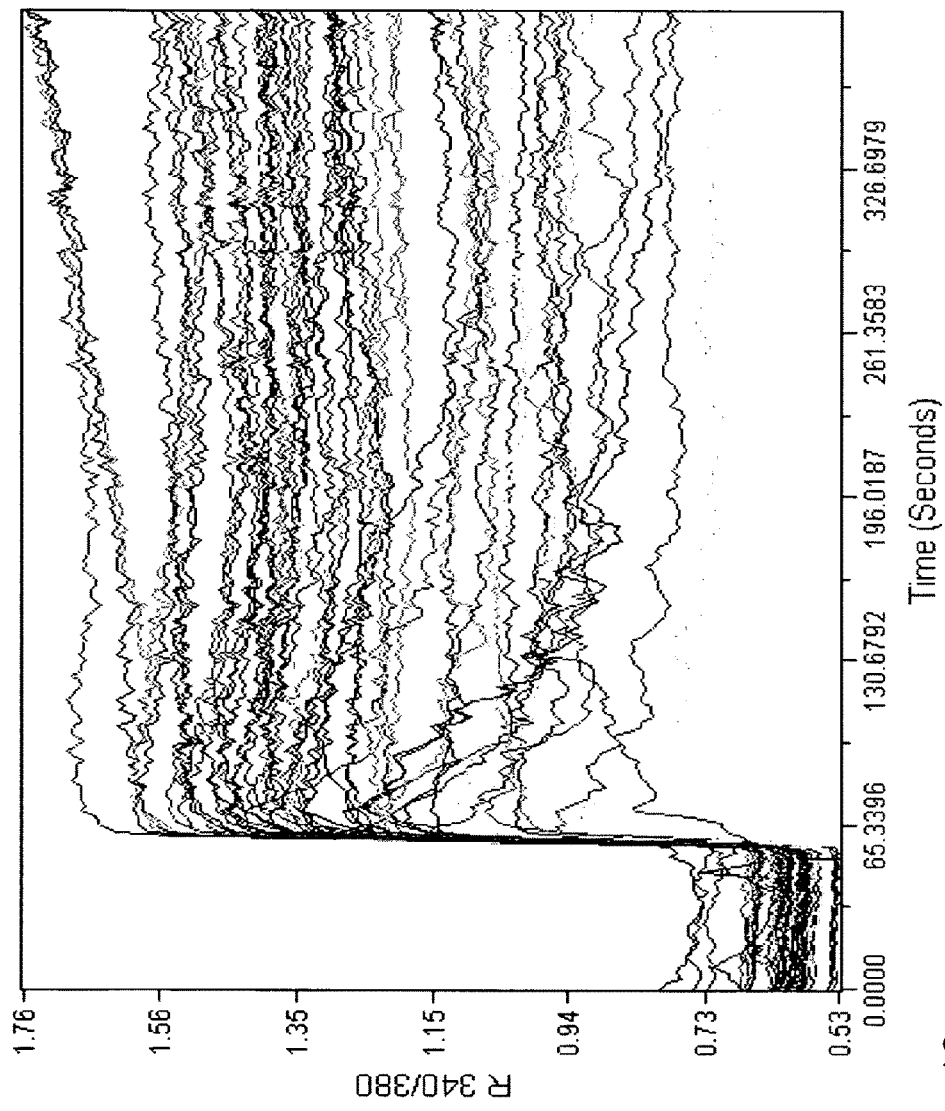
Figure 13:
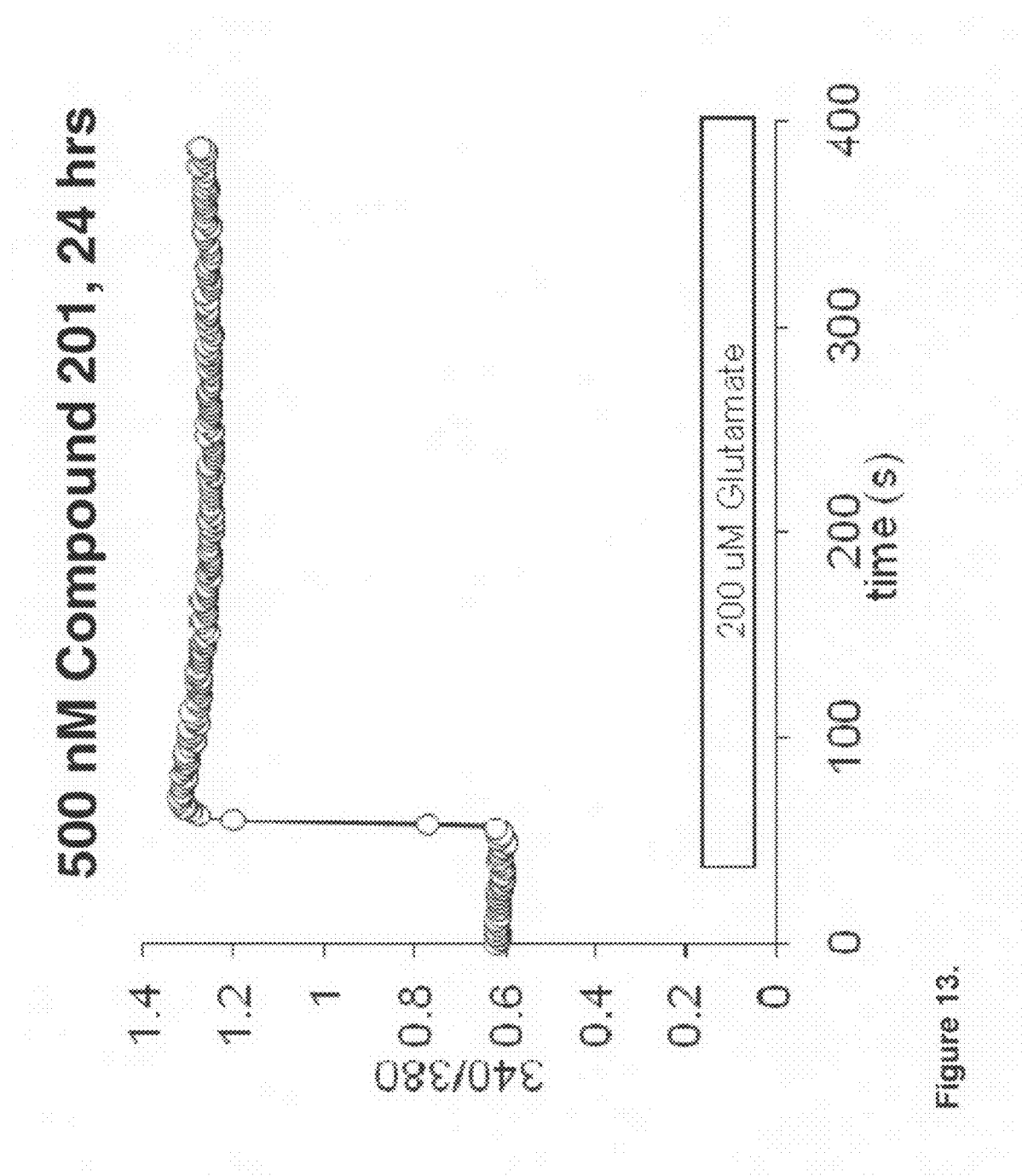
Figure 14:
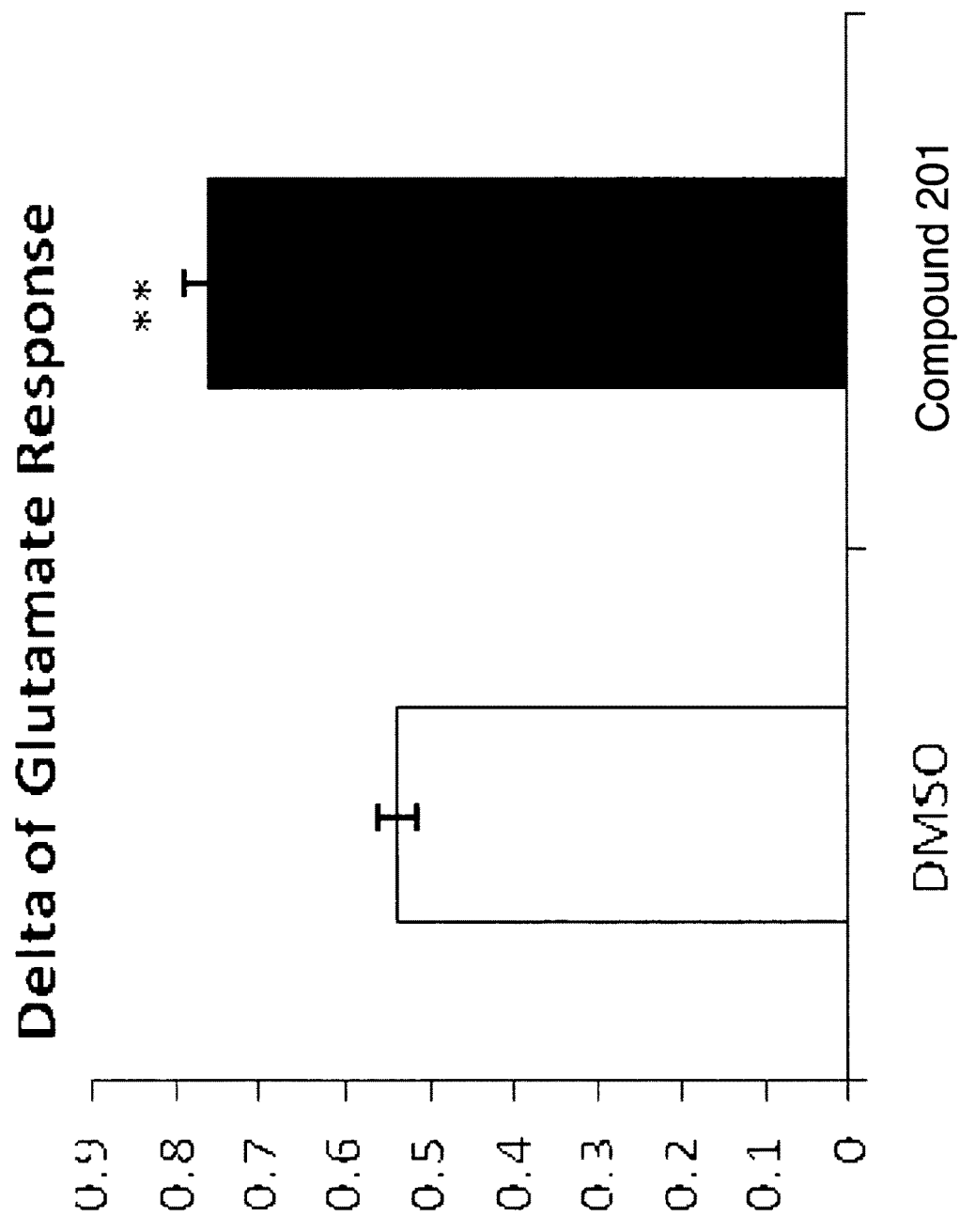

FIG. 11 shows photomicrographs of one field of cells in which change in calcium flux was measured in individual cells (FIG. 12), then averaged (FIG. 13), and the average response was compared to the DMSO control (FIG. 14). The presence of compound 102 significantly enhanced the response to glutamate ($p \leq 0.001$) in this particular study.

FIGS. 15-18. Calcium response to acute exposure to 200 uM glutamate in the presence of 500 nm Compound 201.

Figure 15:
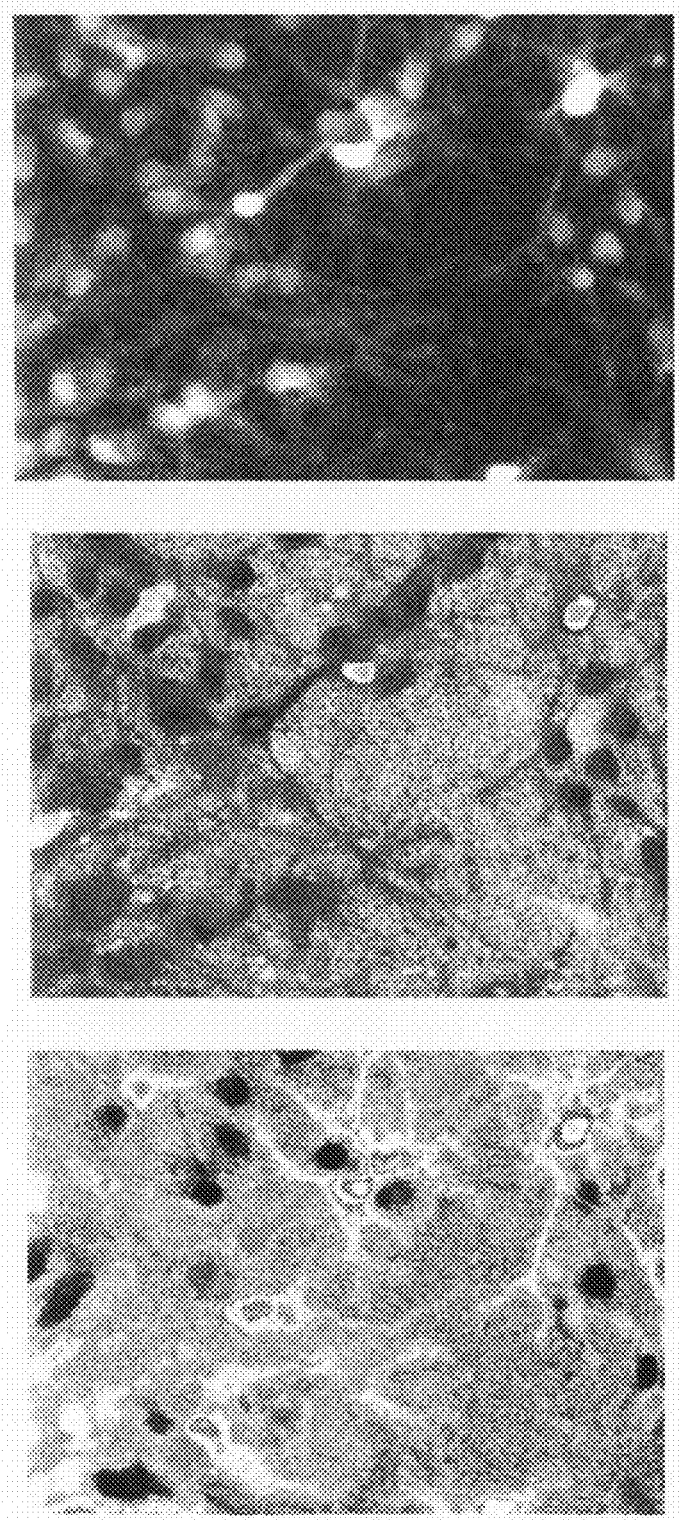
Figure 16:
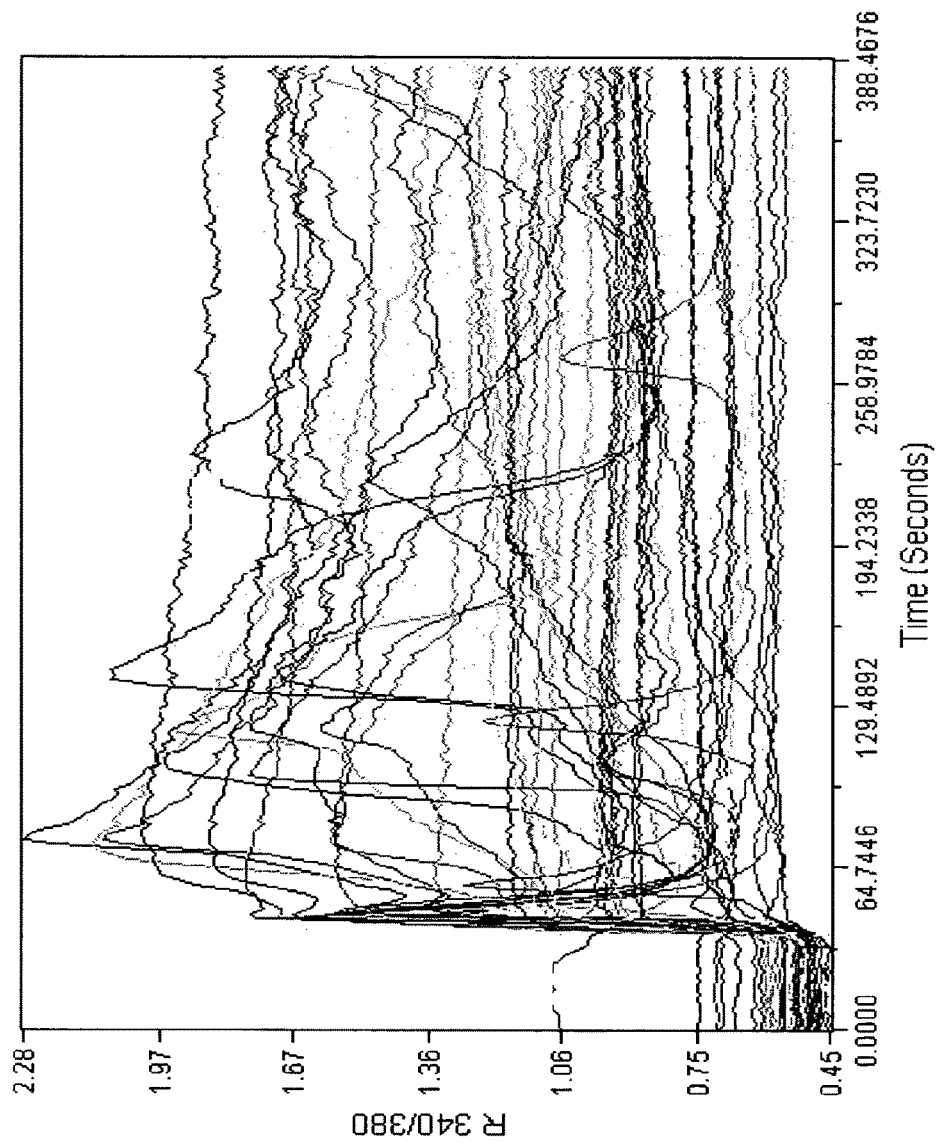
Figure 17:
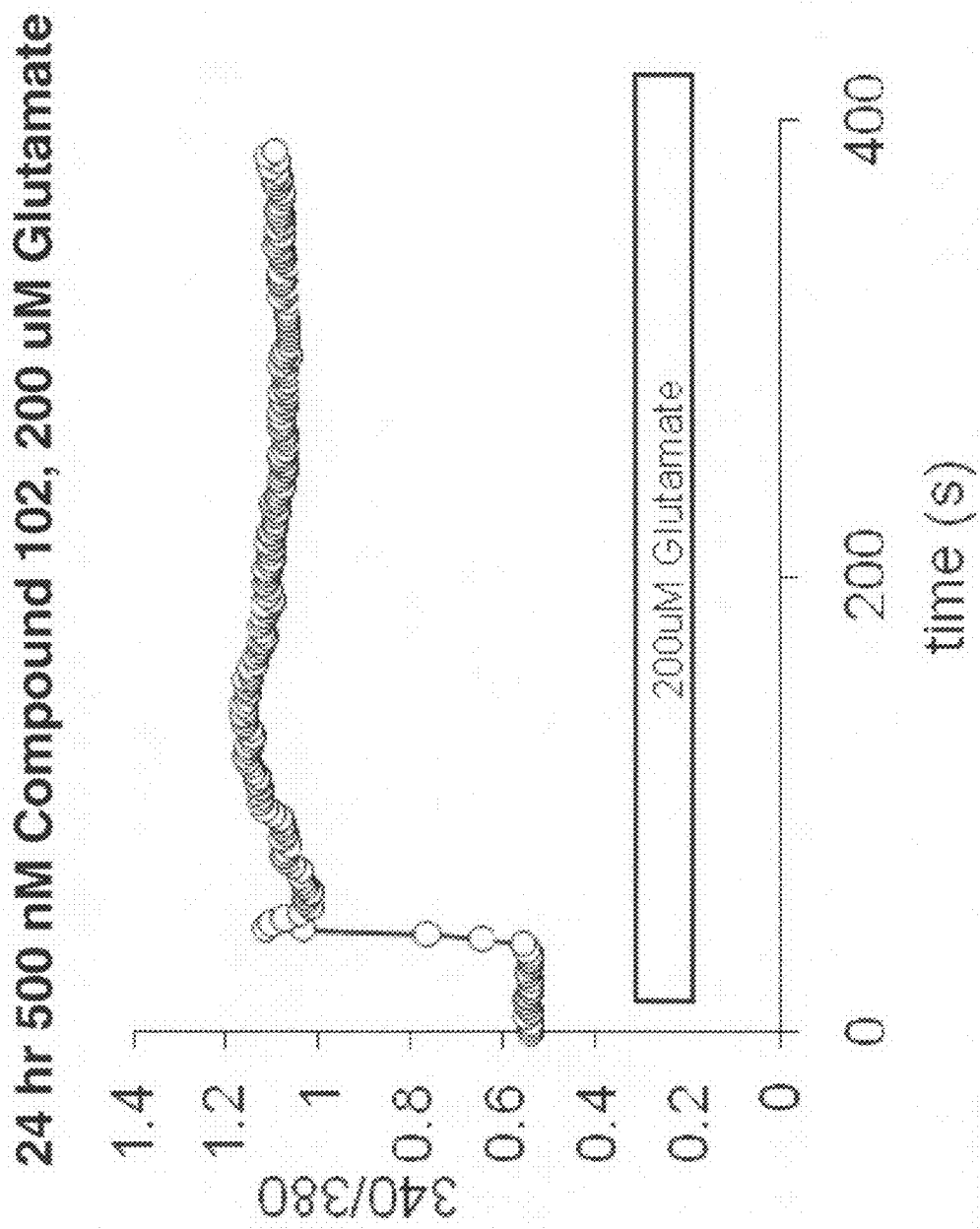
Figure 18:
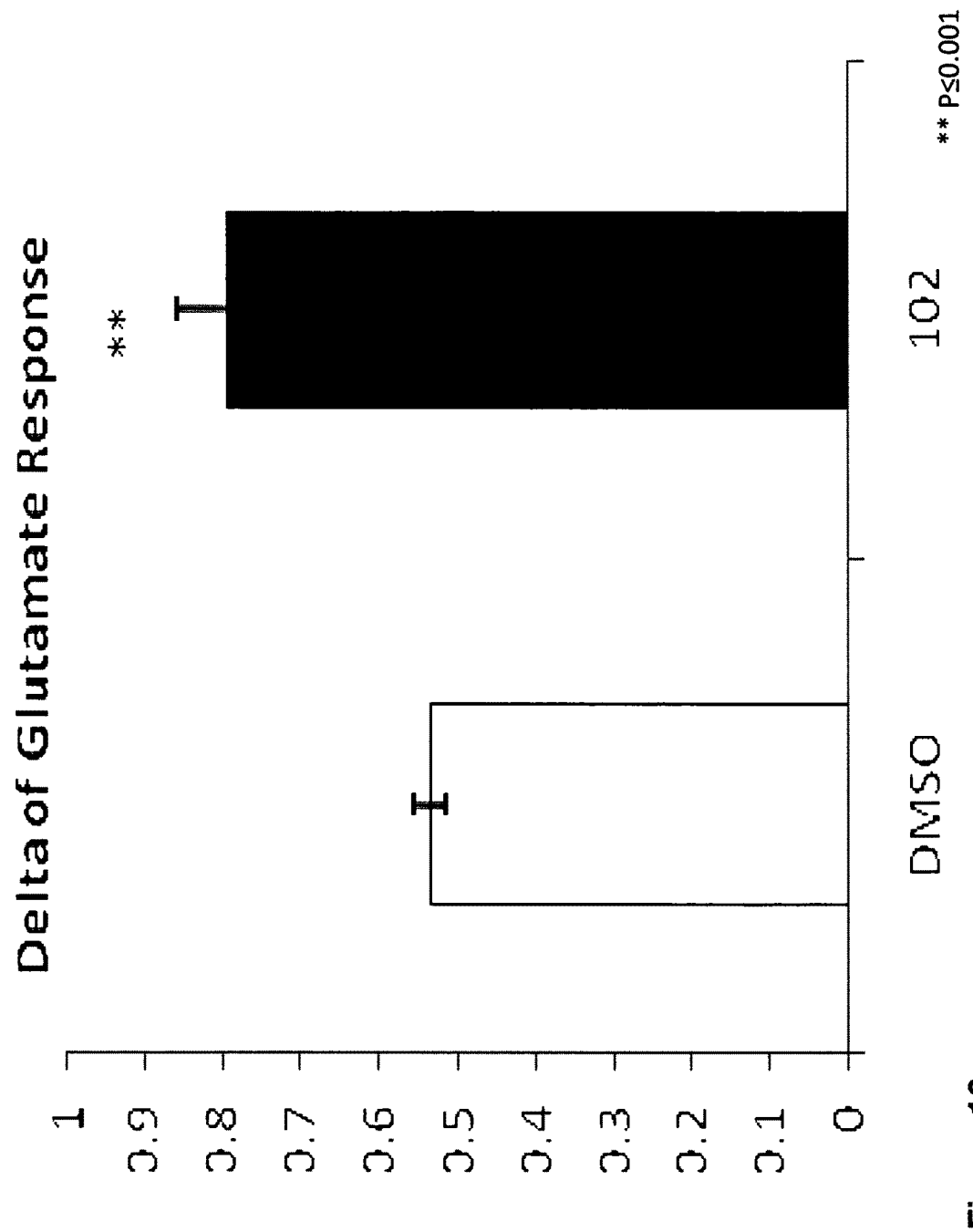

FIG. 15 shows photomicrographs of one field of cells in which change in calcium flux was measured in individual cells (FIG. 16), then averaged (FIG. 17), and the average response was compared to the DMSO control (FIG. 18). The presence of compound 201 significantly enhanced the response to glutamate ($p \leq 0.001$) in this particular study.

Figure 19:
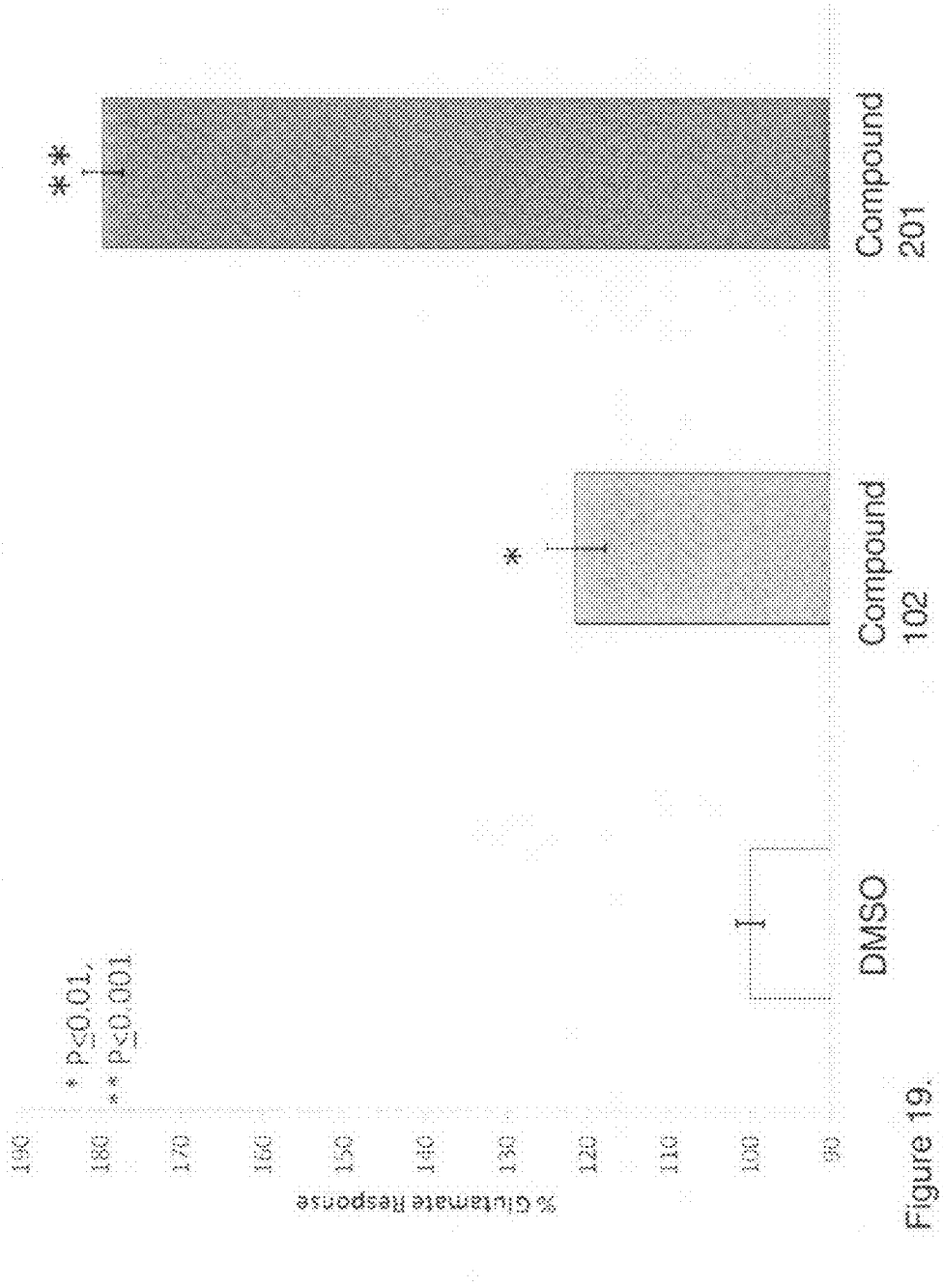

FIG. 19. Bar graph showing the average % increase in response to glutamate exposure of 4 separate experiments.

Compound 201 significantly enhanced the response to glutamate ($p \leq 0.001$) whereas compound 102 was less effective but still had a significant effect of the response at $p \leq 0.01$

DETAILED DESCRIPTION OF THE INVENTION

Embodiments

This invention provides a method of treating a subject with a neurodegenerative disease comprising administering to the subject a compound having the structure

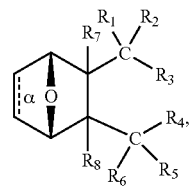

wherein bond α is present or absent;

$R_1$ and $R_2$ is each independently H, $O^-$ or $OR_9$,
where $R_9$ is H, alkyl, alkenyl, alkynyl or aryl, or $R_1$ and $R_2$ together are =O;

$R_3$ and $R_4$ are each different, and each is OH, $O^-$, $OR_9$, SH, $S^-$, $SR_9$,

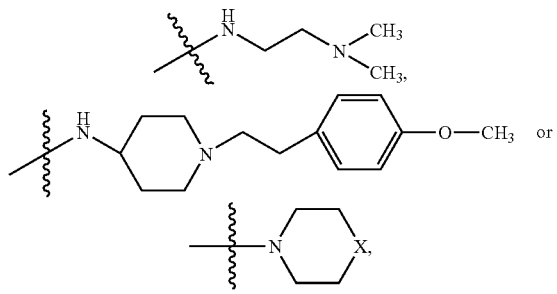

where X is O, S, $NR_{10}$, or $N^+R_{10}R_{10}$,
where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O,

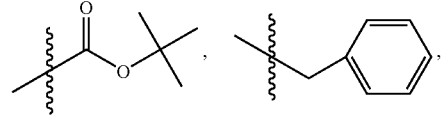

—$CH_2CN$, —$CH_2CO_2R_{11}$, —$CH_2COR_{11}$, —$NHR_{11}$ or —$NH^+(R_{11})_2$, where each $R_{11}$ is independently alkyl, alkenyl or alkynyl, each of which is substituted or unsubstituted, or H;

$R_5$ and $R_6$ is each independently H, OH, or $R_5$ and $R_6$ taken together are =O; and $R_7$ and $R_8$ is each independently H, F, Cl, Br, $SO_2Ph$, $CO_2CH_3$, or $SR_{12}$,
where $R_{12}$ is H, aryl or a substituted or
unsubstituted alkyl, alkenyl or alkynyl, or a salt, enantiomer or zwitterion of the compound, or a compound having the structure

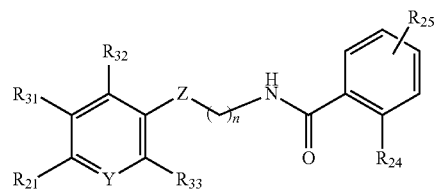

wherein n is 1-10;

Y is C—$R_{30}$ or N, wherein $R_{30}$ is H, OH, SH, F, Cl, $SO_2R_{26}$, $NO_2$, trifluoromethyl, methoxy, or CO—$R_{26}$, wherein $R_{26}$ is alkyl, alkenyl, alkynyl, $C_3$-$C_8$ cycloalkyl, or aryl;

z is

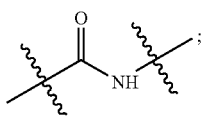

$R_{21}$ is H or $NR_{22}R_{23}$, wherein $R_{22}$ and $R_{23}$ are each independently
H, $C_1$-$C_6$ alkyl, or $C_3$-$C_8$ cycloalkyl;
$R_{24}$ is OH or SH; and
$R_{25}$, $R_{31}$, $R_{32}$, and $R_{33}$ are each independently H, OH, SH, F,
Cl, $SO_2R_{34}$, $NO_2$, trifluoromethyl, methoxy, or CO—$R_{34}$, wherein
$R_{34}$ is alkyl, alkenyl, alkynyl, $C_3$-$C_8$ cycloalkyl, or aryl, or a salt of the compound,
in an amount effective to treat the subject.

In an embodiment of the above method, the compound has the structure

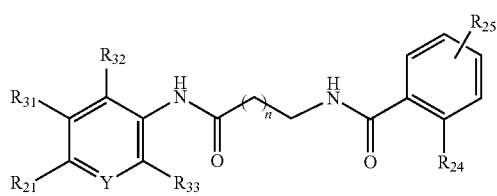

wherein
n is 1-9;
Y is C—$R_{30}$ or N, wherein $R_{30}$ is H, OH, SH, F, Cl, $SO_2R_{26}$, $NO_2$, trifluoromethyl, methoxy, or CO—$R_{26}$, wherein $R_{26}$ is alkyl, alkenyl, alkynyl, $C_3$-$C_8$ cycloalkyl, or aryl;
$R_{21}$ is H or $NR_{22}R_{23}$, wherein $R_{22}$ and $R_{23}$ are each independently H, $C_1$-$C_6$ alkyl, or $C_3$-$C_8$ cycloalkyl;
$R_{24}$ is OH or SH; and
$R_{25}$, $R_{31}$, $R_{32}$, and $R_{33}$ are each independently H, OH, SH, F, Cl, $SO_2R_{34}$, $NO_2$, trifluoromethyl, methoxy, or CO—$R_{34}$, wherein $R_{34}$ is alkyl, alkenyl, alkynyl, $C_3$-$C_8$ cycloalkyl, or aryl.

In another embodiement of the above method, the compound has the structure

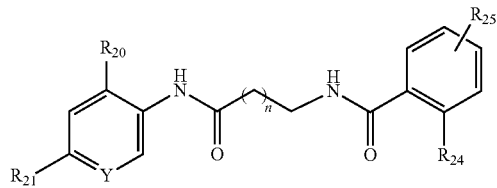

wherein
n is 1-8;
Y is CH or N;
$R_{20}$ is H or OH;
$R_{21}$ is H or $NR_{22}R_{23}$, wherein $R_{22}$ and $R_{23}$ are each independently $C_1$-$C_6$ alkyl or $C_3$-$C_8$ cycloalkyl;
$R_{24}$ is OH or SH; and
$R_{25}$ is H, OH, SH, F, Cl, $SO_2R_{26}$, $NO_2$, trifluoromethyl, methoxy, or CO—$R_{26}$, wherein $R_{26}$ is alkyl, alkenyl, alkynyl, $C_3$-$C_8$ cycloalkyl, or aryl.

In a further embodiment of the above method, the compound has the structure

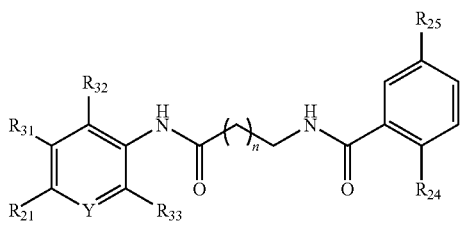

wherein
n is 1-9;
Y is C—$R_{30}$ or N, wherein $R_{30}$ is H, OH, SH, F, Cl, $SO_2R_{26}$, $NO_2$, trifluoromethyl, methoxy, or CO—$R_{26}$, wherein $R_{26}$ is alkyl, alkenyl, alkynyl, $C_3$-$C_8$ cycloalkyl, or aryl;
$R_{21}$ is H or $NR_{22}R_{23}$, wherein $R_{22}$ and $R_{23}$ are each independently H, $C_1$-$C_6$ alkyl, or $C_3$-$C_8$ cycloalkyl;
$R_{24}$ is OH or SH; and
$R_{25}$, $R_{31}$, $R_{32}$, and $R_{33}$ are each independently H, OH, SH, F, Cl, trifluoromethyl, methoxy, or CO—$R_{34}$, wherein $R_{34}$ is alkyl, alkenyl, alkynyl, $C_3$-$C_8$ cycloalkyl, or aryl; In further embodiment, the compound has the structure

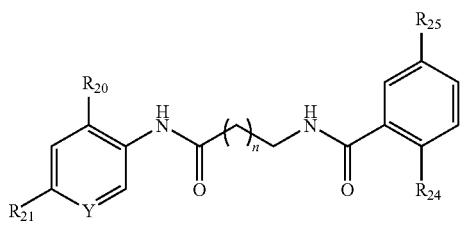

wherein
n is 1-8;
Y is CH or N;
$R_{20}$ is H or OH;
$R_{21}$ is H or $NR_{22}R_{23}$, wherein $R_{22}$ and $R_{23}$ are each independently $C_1$-$C_6$ alkyl or $C_3$-$C_8$ cycloalkyl;
$R_{24}$ is OH or SH; and
$R_{25}$ is H, OH, SH, F, Cl, trifluoromethyl, methoxy, or CO—$R_{26}$, wherein $R_{26}$ is alkyl, alkenyl, alkynyl, or $C_3$-$C_8$ cycloalkyl, or aryl.

In another embodiment, the compound has the structure

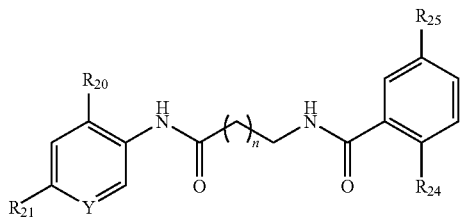

wherein
n is 1-8;
Y is CH or N;
$R_{20}$ is H or OH;
$R_{21}$ is H or $NR_{22}R_{23}$, wherein $R_{22}$ and $R_{23}$ are each independently $C_1$-$C_6$ alkyl or $C_3$-$C_8$ cycloalkyl;

$R_{24}$ is OH or SH; and $R_{25}$ is H, OH, SH, F, Cl, trifluoromethyl, methoxy, or CO—$R_{26}$, wherein $R_{26}$ is alkyl, alkenyl, alkynyl, or $C_3$-$C_8$ cycloalkyl, or aryl.

In an embodiment of the above method, subject is a mammal.

In another embodiment of the above method, the neurodegenerative disease is Alzheimer's disease, Mild Cognitive Impairment, Parkinsons Disease, Frontotemporal Dementia, Dementia, or Lewy Body Dementia. In a further embodiment the neurodegenerative disease is Alzheimer's disease.

Another embodiment of the above method further comprises administering to the subject an NMDA receptor antagonist, an acetylcholinesterase inhibitor, an anti-amyloid antibody, a 5-HT6 antagonist, a gamma secretase inhibitor, a beta secretase inhibitor, or an inhibitor of aggregation of amyloid-β peptide. In another embodiment, the method further comprises administering to the subject a tau aggregation inhibitor.

Examples of known NMDA receptor agonists include, but are not limited to, memantine. Examples of known acetylcholinesterase inhibitors include, but are not limited to, galantamine, rivastigmine, and donapezil. Examples of a tau aggregation inhibitor include, but are not limited to, rember.

In another embodiment of the above method, the neurodegenerative disease is Parkinson's disease.

Another embodiment of the above method further comprises administering to the subject a dopamine receptor agonist.

The invention provides a method for reducing the amount of active GSK-3B in a neural cell comprising contacting the cell with an effective amount of a compound having the structure

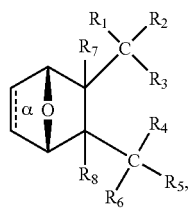

wherein bond α is present or absent;

$R_1$ and $R_2$ is each independently H, O⁻ or OR$_9$, where $R_9$ is H, alkyl, alkenyl, alkynyl or aryl, or $R_1$ and $R_2$ together are =O;

$R_3$ and $R_4$ are each different, and each is OH, O⁻, OR$_9$, SH, S⁻, SR$_9$,

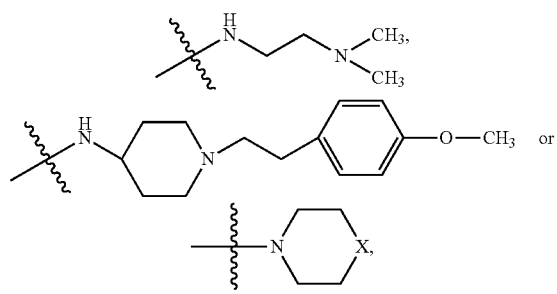

where X is O, S, NR$_{10}$, or N⁺R$_{10}$R$_{10}$, where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O,

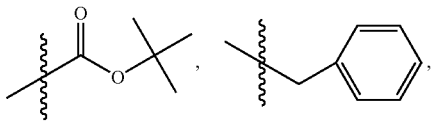

—CH$_2$CN, —CH$_2$CO$_2$R$_{11}$, —CH$_2$COR$_{11}$, —NHR$_{11}$ or —NH⁺(R$_{11}$)$_2$, where each $R_{11}$ is independently alkyl, alkenyl or alkynyl, each of which is substituted or unsubstituted, or H;

$R_5$ and $R_6$ is each independently H, OH, or $R_5$ and $R_6$ taken together are =O; and $R_7$ and $R_8$ is each independently H, F, Cl, Br, SO$_2$Ph, CO$_2$CH$_3$, or SR$_{12}$, where $R_{12}$ is H, aryl or a substituted or unsubstituted alkyl, alkenyl or alkynyl, or a salt, enantiomer or zwitterion of the compound, or a compound having the structure

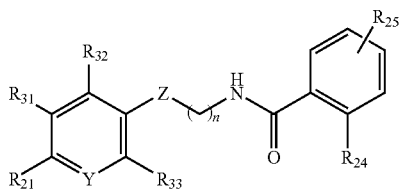

wherein n is 1-10;

Y is C—$R_{30}$ or N, wherein $R_{30}$ is H, OH, SH, F, Cl, SO$_2$R$_{26}$, NO$_2$, trifluoromethyl, methoxy, or CO—$R_{26}$, wherein $R_{26}$ is alkyl, alkenyl, alkynyl, $C_3$-$C_8$ cycloalkyl, or aryl;

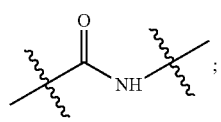

z is $R_{21}$ is H or NR$_{22}$R$_{23}$, wherein $R_{22}$ and $R_{23}$ are each independently H, $C_1$-$C_6$ alkyl, or $C_3$-$C_8$ cycloalkyl;

$R_{24}$ is OH or SH; and $R_{25}$, $R_{31}$, $R_{32}$, and $R_{33}$ are each independently H, OH, SH, F, Cl, SO$_2$R$_{34}$, NO$_2$, trifluoromethyl, methoxy, or CO—$R_{34}$, wherein $R_{34}$ is alkyl, alkenyl, alkynyl, $C_3$-$C_8$ cycloalkyl, or aryl, or a salt of the compound, so as to thereby reduce the amount of GSK-3B in the neural cell.

In an embodiment of the above method, the compound has the structure

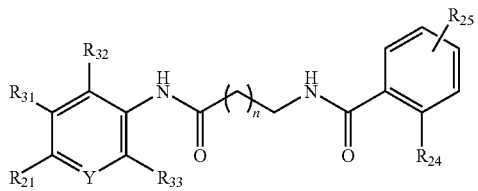

wherein
n is 1-9;
Y is C—$R_{30}$ or N, wherein $R_{30}$ is H, OH, SH, F, Cl, $SO_2R_{26}$, $NO_2$, trifluoromethyl, methoxy, or CO—$R_{26}$, wherein $R_{26}$ is alkyl, alkenyl, alkynyl, $C_3$-$C_8$ cycloalkyl, or aryl;
$R_{21}$ is H or $NR_{22}R_{23}$, wherein $R_{22}$ and $R_{23}$ are each independently H, $C_1$-$C_6$ alkyl, or $C_3$-$C_8$ cycloalkyl;
$R_{24}$ is OH or SH; and
$R_{25}$, $R_{31}$, $R_{32}$, and $R_{33}$ are each independently H, OH, SH, F, Cl, $SO_2R_{34}$, $NO_2$, trifluoromethyl, methoxy, or CO—$R_{34}$, wherein
$R_{34}$ is alkyl, alkenyl, alkynyl, $C_3$-$C_8$ cycloalkyl, or aryl.

In another embodiement of the above method, the compound has the structure

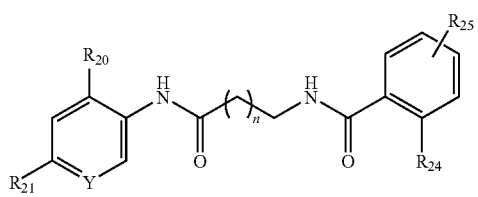

wherein
n is 1-8;
Y is CH or N;
$R_{20}$ is H or OH;
$R_{21}$ is H or $NR_{22}R_{23}$, wherein $R_{22}$ and $R_{23}$ are each independently $C_1$-$C_6$ alkyl or $C_3$-$C_8$ cycloalkyl;
$R_{24}$ is OH or SH; and
$R_{25}$ is H, OH, SH, F, Cl, $SO_2R_{26}$, $NO_2$, trifluoromethyl, methoxy, or CO—$R_{26}$, wherein $R_{26}$ is alkyl, alkenyl, alkynyl, $C_3$-$C_8$ cycloalkyl, or aryl.

In a further embodiment of the above method, the compound has the structure

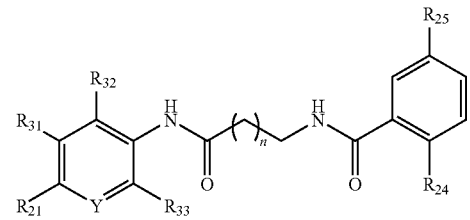

wherein
n is 1-9;
Y is C—$R_{30}$ or N, wherein $R_{30}$ is H, OH, SH, F, Cl, $SO_2R_{26}$, $NO_2$, trifluoromethyl, methoxy, or CO—$R_{26}$, wherein $R_{26}$ is alkyl, alkenyl, alkynyl, $C_3$-$C_8$ cycloalkyl, or aryl;
$R_{21}$ is H or $NR_{22}R_{23}$, wherein $R_{22}$ and $R_{23}$ are each independently H, $C_1$-$C_6$ alkyl, or $C_3$-$C_8$ cycloalkyl;
$R_{24}$ is OH or SH; and
$R_{25}$, $R_{31}$, $R_{32}$, and $R_{33}$ are each independently H, OH, SH, F, Cl, trifluoromethyl, methoxy, or CO—$R_{34}$, wherein $R_{34}$ is alkyl, alkenyl, alkynyl, $C_3$-$C_8$ cycloalkyl, or aryl;

In further embodiment, the compound has the structure

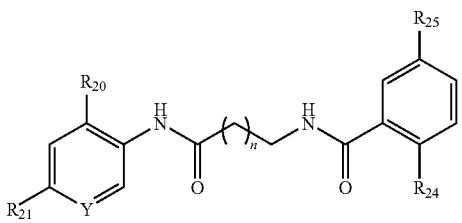

wherein
n is 1-8;
Y is CH or N;
$R_{20}$ is H or OH;
$R_{21}$ is H or $NR_{22}R_{23}$, wherein $R_{22}$ and $R_{23}$ are each independently $C_1$-$C_6$ alkyl or $C_3$-$C_8$ cycloalkyl;
$R_{24}$ is OH or SH; and
$R_{25}$ is H, OH, SH, F, Cl, trifluoromethyl, methoxy, or CO—$R_{26}$, wherein $R_{26}$ is alkyl, alkenyl, alkynyl, or $C_3$-$C_8$ cycloalkyl, or aryl.

In another embodiment, the compound has the structure

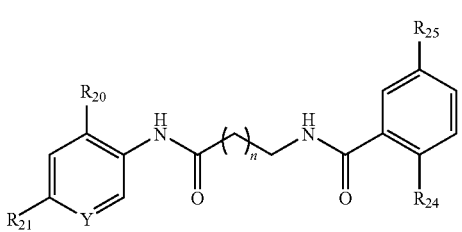

wherein
n is 1-8;
Y is CH or N;
$R_{20}$ is H or OH;
$R_{21}$ is H or $NR_{22}R_{23}$, wherein $R_{22}$ and $R_{23}$ are each independently $C_1$-$C_6$ alkyl or $C_3$-$C_8$ cycloalkyl;
$R_{24}$ is OH or SH; and
$R_{25}$ is H, OH, SH, F, Cl, trifluoromethyl, methoxy, or CO—$R_{26}$, wherein $R_{26}$ is alkyl, alkenyl, alkynyl, or $C_3$-$C_8$ cycloalkyl, or aryl.

The invention provides a method for increasing the amount of phosphorylated Akt in a neural cell comprising contacting the neural cell with an effective amount of a compound having the structure

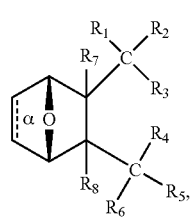

wherein bond α is present or absent;

$R_1$ and $R_2$ is each independently H, O⁻ or $OR_9$,
where $R_9$ is H, alkyl, alkenyl, alkynyl or aryl, or $R_1$ and $R_2$ together are =O;

$R_3$ and $R_4$ are each different, and each is OH, O⁻, $OR_9$, SH, S⁻, $SR_9$,

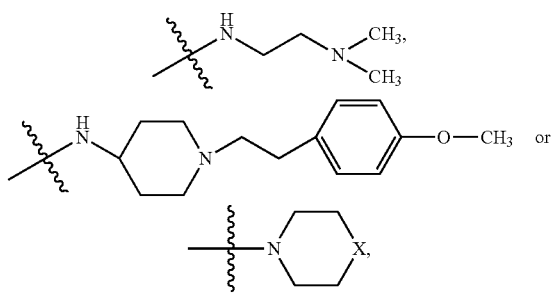

where X is O, S, $NR_{10}$, or $N^+R_{10}R_{10}$,
where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O,

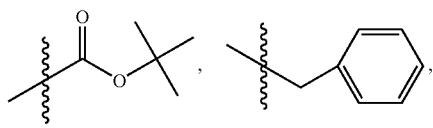

—$CH_2CN$, —$CH_2CO_2R_{11}$, —$CH_2COR_{11}$, —$NHR_{11}$ or —$NH^+(R_{11})_2$, where each $R_{11}$ is independently alkyl, alkenyl or alkynyl, each of which is substituted or unsubstituted, or H;

$R_5$ and $R_6$ is each independently H, OH, or $R_5$ and $R_6$ taken together are =O; and $R_7$ and $R_8$ is each independently H, F, Cl, Br, $SO_2Ph$, $CO_2CH_3$, or $SR_{12}$,
where $R_{12}$ is H, aryl or a substituted or unsubstituted alkyl, alkenyl or alkynyl, or a salt, enantiomer or zwitterion of the compound, or a compound having the structure

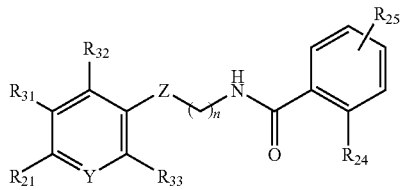

wherein n is 1-10;

Y is C—$R_{30}$ or N, wherein $R_{30}$ is H, OH, SH, F, Cl, $SO_2R_{26}$, $NO_2$, trifluoromethyl, methoxy, or CO—$R_{26}$, wherein $R_{26}$ is alkyl, alkenyl, alkynyl, $C_3$-$C_8$ cycloalkyl, or aryl;

z is

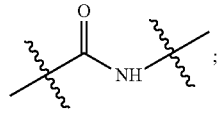

$R_{21}$ is H or $NR_{22}R_{23}$, wherein $R_{22}$ and $R_{23}$ are each independently H, $C_1$-$C_6$ alkyl, or $C_3$-$C_8$ cycloalkyl;

$R_{24}$ is OH or SH; and $R_{25}$, $R_{31}$, $R_{32}$, and $R_{33}$ are each independently H, OH, SH, F, Cl, $SO_2R_{34}$, $NO_2$, trifluoromethyl, methoxy, or CO—$R_{34}$, wherein $R_{34}$ is alkyl, alkenyl, alkynyl, $C_3$-$C_8$ cycloalkyl, or aryl, or a salt of the compound, so as to thereby increase the amount of phosphorylated Akt in the neural cell.

In an embodiment of the above method, the compound has the structure

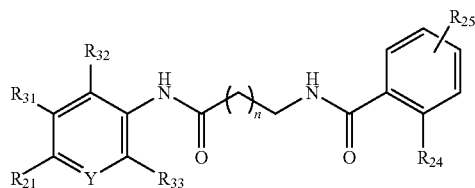

wherein n is 1-9;

Y is C—$R_{30}$ or N, wherein $R_{30}$ is H, OH, SH, F, Cl, $SO_2R_{26}$, $NO_2$, trifluoromethyl, methoxy, or CO—$R_{26}$, wherein $R_{26}$ is alkyl, alkenyl, alkynyl, $C_3$-$C_8$ cycloalkyl, or aryl;

$R_{21}$ is H or $NR_{22}R_{23}$, wherein $R_{22}$ and $R_{23}$ are each independently H, $C_1$-$C_6$ alkyl, or $C_3$-$C_8$ cycloalkyl;

$R_{24}$ is OH or SH; and $R_{25}$, $R_{31}$, $R_{32}$, and $R_{33}$ are each independently H, OH, SH, F, Cl, $SO_2R_{34}$, $NO_2$, trifluoromethyl, methoxy, or CO—$R_{34}$, wherein $R_{34}$ is alkyl, alkenyl, alkynyl, $C_3$-$C_8$ cycloalkyl, or aryl.

In another embodiement of the above method, the compound has the structure

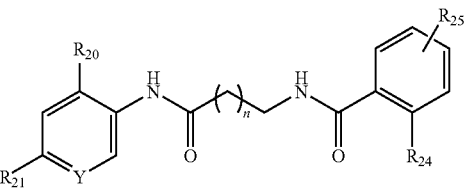

wherein n is 1-8;

Y is CH or N;

$R_{20}$ is H or OH;

$R_{21}$ is H or $NR_{22}R_{23}$, wherein $R_{22}$ and $R_{23}$ are each independently $C_1$-$C_6$ alkyl or $C_3$-$C_8$ cycloalkyl;

$R_{24}$ is OH or SH; and $R_{25}$ is H, OH, SH, F, Cl, $SO_2R_{26}$, $NO_2$, trifluoromethyl, methoxy, or CO—$R_{26}$, wherein $R_{26}$ is alkyl, alkenyl, alkynyl, $C_3$-$C_8$ cycloalkyl, or aryl.

In a further embodiment of the above method, the compound has the structure

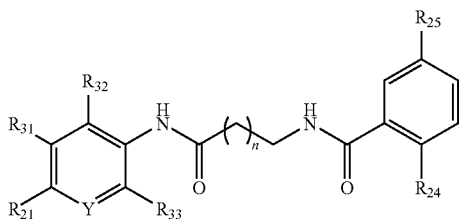

wherein
n is 1-9;
Y is C—$R_{30}$ or N, wherein $R_{30}$ is H, OH, SH, F, Cl, $SO_2R_{26}$, $NO_2$, trifluoromethyl, methoxy, or CO—$R_{26}$, wherein $R_{26}$ is alkyl, alkenyl, alkynyl, $C_3$-$C_8$ cycloalkyl, or aryl;
$R_{21}$ is H or $NR_{22}R_{23}$, wherein $R_{22}$ and $R_{23}$ are each independently H, $C_1$-$C_6$ alkyl, or $C_3$-$C_8$ cycloalkyl;
$R_{24}$ is OH or SH; and
$R_{25}$, $R_{31}$, $R_{32}$, and $R_{33}$ are each independently H, OH, SH, F, Cl, trifluoromethyl, methoxy, or CO—$R_{34}$, wherein $R_{34}$ is alkyl, alkenyl, alkynyl, $C_3$-$C_8$ cycloalkyl, or aryl; In further embodiment, the compound has the structure

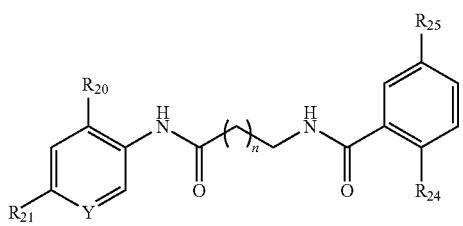

wherein
n is 1-8;
Y is CH or N;
$R_{20}$ is H or OH;
$R_{21}$ is H or $NR_{22}R_{23}$, wherein $R_{22}$ and $R_{23}$ are each independently $C_1$-$C_6$ alkyl or $C_3$-$C_8$ cycloalkyl;
$R_{24}$ is OH or SH; and
$R_{25}$ is H, OH, SH, F, Cl, trifluoromethyl, methoxy, or CO—$R_{26}$, wherein $R_{26}$ is alkyl, alkenyl, alkynyl, or $C_3$-$C_8$ cycloalkyl, or aryl.
In another embodiment, the compound has the structure

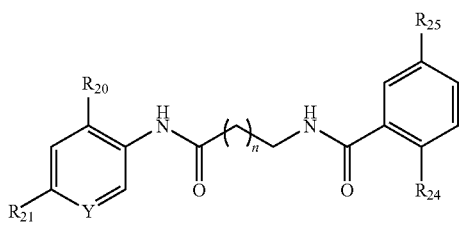

wherein
n is 1-8;
Y is CH or N;
$R_{20}$ is H or OH;
$R_{21}$ is H or $NR_{22}R_{23}$, wherein $R_{22}$ and $R_{23}$ are each independently $C_1$-$C_6$ alkyl or $C_3$-$C_8$ cycloalkyl;
$R_{24}$ is OH or SH; and
$R_{25}$ is H, OH, SH, F, Cl, trifluoromethyl, methoxy, or CO—$R_{26}$, wherein $R_{26}$ is alkyl, alkenyl, alkynyl, or $C_3$-$C_8$ cycloalkyl, or aryl.

The invention provides a method for reducing the phosphorylation of Tau protein in a cell, comprising contacting the cell with an effective amount of a compound having the structure

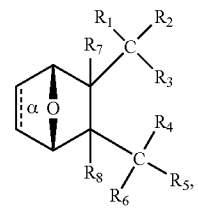

wherein
bond α is present or absent;
$R_1$ and $R_2$ is each independently H, $O^-$ or $OR_9$,
    where $R_9$ is H, alkyl, alkenyl, alkynyl or aryl, or $R_1$ and $R_2$ together are =O;
$R_3$ and $R_4$ are each different, and each is OH, $O^-$, $OR_9$, SH, $S^{31}$, $SR_9$,

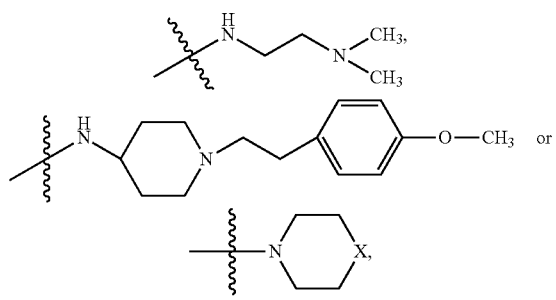

where X is O, S, $NR_{10}$, or $N^+R_{10}R_{10}$,
    where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O,

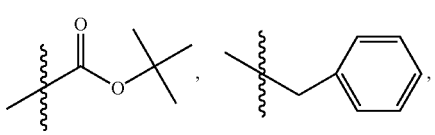

—$CH_2CN$, —$CH_2CO_2R_{11}$, —$CH_2COR_{11}$, —$NHR_{11}$ or —$NH^+(R_{11})_2$, where each $R_1$1 is independently alkyl, alkenyl or alkynyl, each of which is substituted or unsubstituted, or H;
$R_5$ and $R_6$ is each independently H, OH, or $R_5$ and $R_6$ taken together are =O; and
$R_7$ and $R_8$ is each independently H, F, Cl, Br, $SO_2Ph$, $CO_2CH_3$, or $SR_{12}$,
    where $R_{12}$ is H, aryl or a substituted or unsubstituted alkyl, alkenyl or alkynyl, or a salt, enantiomer or zwitterion of the compound, or a compound having the structure

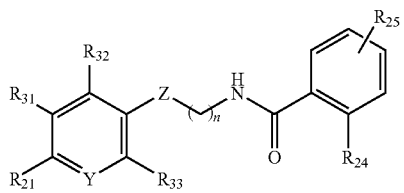

wherein n is 1-10;

Y is C—$R_{30}$ or N, wherein $R_{30}$ is H, OH, SH, F, Cl, $SO_2R_{26}$, $NO_2$, trifluoromethyl, methoxy, or CO—$R_{26}$, wherein $R_{26}$ is alkyl, alkenyl, alkynyl, $C_3$-$C_8$ cycloalkyl, or aryl;

z is

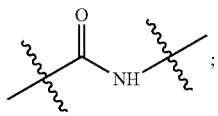

$R_{21}$ is H or $NR_{22}R_{23}$, wherein $R_{22}$ and $R_{23}$ are each independently H, $C_1$-$C_6$ alkyl, or $C_3$-$C_8$ cycloalkyl;

$R_{24}$ is OH or SH; and $R_{25}$, $R_{31}$, $R_{32}$, and $R_{33}$ are each independently H, OH, SH, F, Cl, $SO_2R_{34}$, $NO_2$, trifluoromethyl, methoxy, or CO—$R_{34}$, wherein $R_{34}$ is alkyl, alkenyl, alkynyl, $C_3$-$C_8$ cycloalkyl, or aryl, or a salt of the compound, so as to thereby reduce the phosphorylation of tau in the cell.

In an embodiment of the above method, the compound has the structure

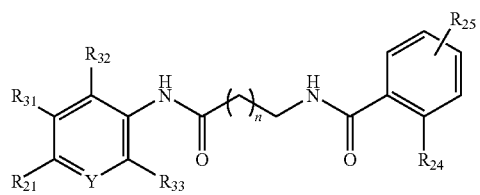

wherein n is 1-9;

Y is C—$R_{30}$ or N, wherein $R_{30}$ is H, OH, SH, F, Cl, $SO_2R_{26}$, $NO_2$, trifluoromethyl, methoxy, or CO—$R_{26}$, wherein $R_{26}$ is alkyl, alkenyl, alkynyl, $C_3$-$C_8$ cycloalkyl, or aryl;

$R_{21}$ is H or $NR_{22}R_{23}$, wherein $R_{22}$ and $R_{23}$ are each independently H, $C_1$-$C_6$ alkyl, or $C_3$-$C_8$ cycloalkyl;

$R_{24}$ is OH or SH; and $R_{25}$, $R_{31}$, $R_{32}$, and $R_{33}$ are each independently H, OH, SH, F, Cl, $SO_2R_{34}$, $NO_2$, trifluoromethyl, methoxy, or CO—$R_{34}$, wherein $R_{34}$ is alkyl, alkenyl, alkynyl, $C_3$-$C_8$ cycloalkyl, or aryl.

In another embodiement of the above method, the compound has the structure

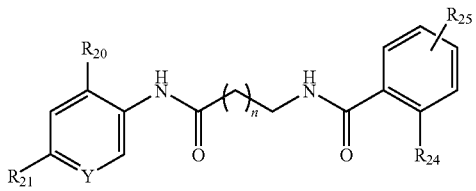

wherein n is 1-8;

Y is CH or N;

$R_{20}$ is H or OH;

$R_{21}$ is H or $NR_{22}R_{23}$, wherein $R_{22}$ and $R_{23}$ are each independently $C_1$-$C_6$ alkyl or $C_3$-$C_8$ cycloalkyl;

$R_{24}$ is OH or SH; and $R_{25}$ is H, OH, SH, F, Cl, $SO_2R_{26}$, $NO_2$, trifluoromethyl, methoxy, or CO—$R_{26}$, wherein $R_{26}$ is alkyl, alkenyl, alkynyl, $C_3$-$C_8$ cycloalkyl, or aryl.

In a further embodiment of the above method, the compound has the structure

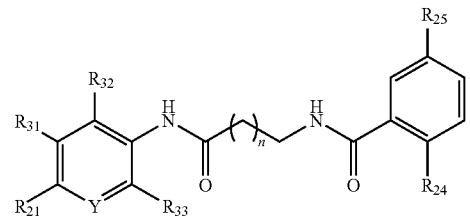

wherein n is 1-9;

Y is C—$R_{30}$ or N, wherein $R_{30}$ is H, OH, SH, F, Cl, $SO_2R_{26}$, $NO_2$, trifluoromethyl, methoxy, or CO—$R_{26}$, wherein $R_{26}$ is alkyl, alkenyl, alkynyl, $C_3$-$C_8$ cycloalkyl, or aryl;

$R_{21}$ is H or $NR_{22}R_{23}$, wherein $R_{22}$ and $R_{23}$ are each independently H, $C_1$-$C_6$ alkyl, or $C_3$-$C_8$ cycloalkyl;

$R_{24}$ is OH or SH; and $R_{25}$, $R_{31}$, $R_{32}$, and $R_{33}$ are each independently H, OH, SH, F, Cl, trifluoromethyl, methoxy, or CO—$R_{34}$, wherein $R_{34}$ is alkyl, alkenyl, alkynyl, $C_3$-$C_8$ cycloalkyl, or aryl; In further embodiment, the compound has the structure

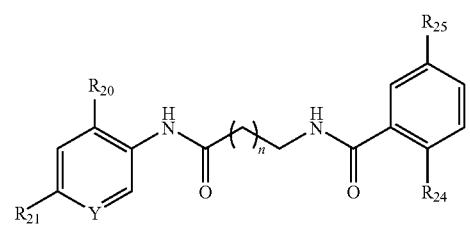

wherein n is 1-8;

Y is CH or N;

$R_{20}$ is H or OH;

$R_{21}$ is H or $NR_{22}R_{23}$, wherein $R_{22}$ and $R_{23}$ are each independently $C_1$-$C_6$ alkyl or $C_3$-$C_8$ cycloalkyl;

$R_{24}$ is OH or SH; and $R_{25}$ is H, OH, SH, F, Cl, trifluoromethyl, methoxy, or CO—$R_{26}$, wherein $R_{26}$ is alkyl, alkenyl, alkynyl, or $C_3$-$C_8$ cycloalkyl, or aryl.

In another embodiment, the compound has the structure

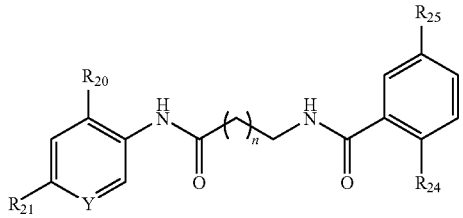

wherein
n is 1-8;
Y is CH or N;
$R_{20}$ is H or OH;
$R_{21}$ is H or $NR_{22}R_{23}$, wherein $R_{22}$ and $R_{23}$ are each independently $C_1$-$C_6$ alkyl or $C_3$-$C_8$ cycloalkyl;
$R_{24}$ is OH or SH; and
$R_{25}$ is H, OH, SH, F, Cl, trifluoromethyl, methoxy, or CO—$R_{26}$, wherein $R_{26}$ is alkyl, alkenyl, alkynyl, or $C_3$-$C_8$ cycloalkyl, or aryl.

The invention provides a method for reducing the aggregation of Tau protein in a cell comprising contacting the cell with an effective amount of a compound having the structure

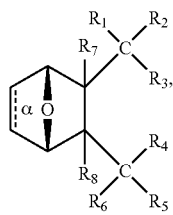

wherein
bond α is present or absent;
$R_1$ and $R_2$ is each independently H, O⁻ or $OR_9$,
where $R_9$ is H, alkyl, alkenyl, alkynyl or aryl, or $R_1$ and $R_2$ together are =O;
$R_3$ and $R_4$ are each different, and each is OH, O⁻, $OR_9$, SH, S⁻, $SR_9$,

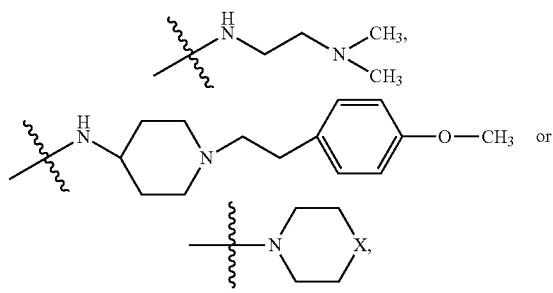

where X is O, S, $NR_{10}$, or $N^+R_{10}R_{10}$,
where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O,

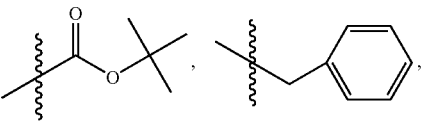

—$CH_2CN$, —$CH_2CO_2R_{11}$, —$CH_2COR_{11}$, —$NHR_{11}$ or —$NH^+(R_{11})_2$, where each $R_11$ is independently alkyl, alkenyl or alkynyl, each of which is substituted or unsubstituted, or H;
$R_5$ and $R_6$ is each independently H, OH, or $R_5$ and $R_6$ taken together are =O; and
$R_7$ and $R_8$ is each independently H, F, Cl, Br, $SO_2Ph$, $CO_2CH_3$, or $SR_{12}$,
where $R_{12}$ is H, aryl or a substituted or unsubstituted alkyl, alkenyl or alkynyl,
or a salt, enantiomer or zwitterion of the compound, or a compound having the structure

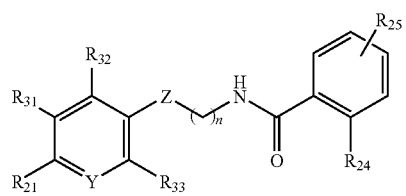

wherein
n is 1-10;
Y is C—$R_{30}$ or N, wherein $R_{30}$ is H, OH, SH, F, Cl, $SO_2R_{26}$, $NO_2$, trifluoromethyl, methoxy, or CO—$R_{26}$, wherein $R_{26}$ is alkyl, alkenyl, alkynyl, $C_3$-$C_8$ cycloalkyl, or aryl;
Z is

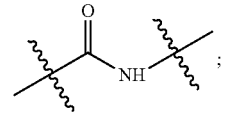

$R_{21}$ is H or $NR_{22}R_{23}$, wherein $R_{22}$ and $R_{23}$ are each independently H, $C_1$-$C_6$ alkyl, or $C_3$-$C_8$ cycloalkyl;
$R_{24}$ is OH or SH; and
$R_{25}$, $R_{31}$, $R_{32}$, and $R_{33}$ are each independently H, OH, SH, F, Cl, $SO_2R_{34}$, $NO_2$, trifluoromethyl, methoxy, or CO—$R_{34}$, wherein
$R_{34}$ is alkyl, alkenyl, alkynyl, $C_3$-$C_8$ cycloalkyl, or aryl, or a salt of the compound,
so as to thereby inhibit the aggregation of Tau in the cell.

In an embodiment of the above method, the compound has the structure

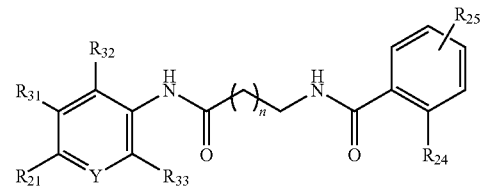

wherein
n is 1-9;

Y is C—$R_{30}$ or N, wherein $R_{30}$ is H, OH, SH, F, Cl, $SO_2R_{26}$, $NO_2$, trifluoromethyl, methoxy, or CO—$R_{26}$, wherein $R_{26}$ is alkyl, alkenyl, alkynyl, $C_3$-$C_8$ cycloalkyl, or aryl;

$R_{21}$ is H or $NR_{22}R_{23}$, wherein $R_{22}$ and $R_{23}$ are each independently H, $C_1$-$C_6$ alkyl, or $C_3$-$C_8$ cycloalkyl;

$R_{24}$ is OH or SH; and $R_{25}$, $R_{31}$, $R_{32}$, and $R_{33}$ are each independently H, OH, SH, F, Cl, $SO_2R_{34}$, $NO_2$, trifluoromethyl, methoxy, or CO—$R_{34}$, wherein $R_{34}$ is alkyl, alkenyl, alkynyl, $C_3$-$C_8$ cycloalkyl, or aryl.

In another embodiement of the above method, the compound has the structure

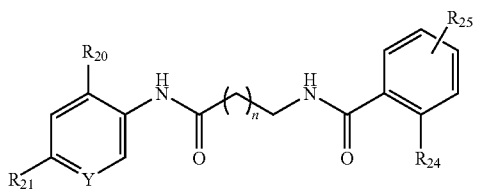

wherein n is 1-8;

Y is CH or N;

$R_{20}$ is H or OH;

$R_{21}$ is H or $NR_{22}R_{23}$, wherein $R_{22}$ and $R_{23}$ are each independently $C_1$-$C_6$ alkyl or $C_3$-$C_8$ cycloalkyl;

$R_{24}$ is OH or SH; and $R_{25}$ is H, OH, SH, F, Cl, $SO_2R_{26}$, $NO_2$, trifluoromethyl, methoxy, or CO—$R_{26}$, wherein $R_{26}$ is alkyl, alkenyl, alkynyl, $C_3$-$C_8$ cycloalkyl, or aryl.

In a further embodiment of the above method, the compound has the structure

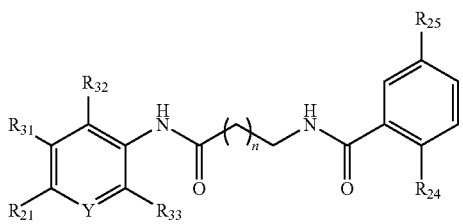

wherein n is 1-9;

Y is C—$R_{30}$ or N, wherein $R_{30}$ is H, OH, SH, F, Cl, $SO_2R_{26}$, $NO_2$, trifluoromethyl, methoxy, or CO—$R_{26}$, wherein $R_{26}$ is alkyl, alkenyl, alkynyl, $C_3$-$C_8$ cycloalkyl, or aryl;

$R_{21}$ is H or $NR_{22}R_{23}$, wherein $R_{22}$ and $R_{23}$ are each independently H, $C_1$-$C_6$ alkyl, or $C_3$-$C_8$ cycloalkyl;

$R_{24}$ is OH or SH; and $R_{25}$, $R_{31}$, $R_{32}$, and $R_{33}$ are each independently H, OH, SH, F, Cl, trifluoromethyl, methoxy, or CO—$R_{34}$, wherein $R_{34}$ is alkyl, alkenyl, alkynyl, $C_3$-$C_8$ cycloalkyl, or aryl; In further embodiment, the compound has the structure

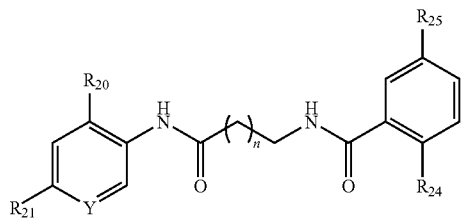

wherein n is 1-8;

Y is CH or N;

$R_{20}$ is H or OH;

$R_{21}$ is H or $NR_{22}R_{23}$, wherein $R_{22}$ and $R_{23}$ are each independently $C_1$-$C_6$ alkyl or $C_3$-$C_8$ cycloalkyl;

$R_{24}$ is OH or SH; and $R_{25}$ is H, OH, SH, F, Cl, trifluoromethyl, methoxy, or CO—$R_{26}$, wherein $R_{26}$ is alkyl, alkenyl, alkynyl, or $C_3$-$C_8$ cycloalkyl, or aryl.

In another embodiment, the compound has the structure

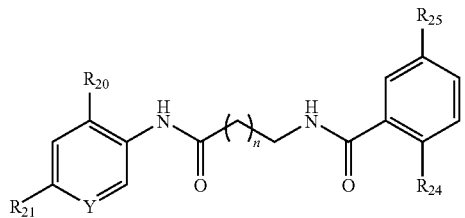

wherein n is 1-8;

Y is CH or N;

$R_{20}$ is H or OH;

$R_{21}$ is H or $NR_{22}R_{23}$, wherein $R_{22}$ and $R_{23}$ are each independently $C_1$-$C_6$ alkyl or $C_3$-$C_8$ cycloalkyl;

$R_{24}$ is OH or SH; and $R_{25}$ is H, OH, SH, F, Cl, trifluoromethyl, methoxy, or CO—$R_{26}$, wherein $R_{26}$ is alkyl, alkenyl, alkynyl, or $C_3$-$C_8$ cycloalkyl, or aryl.

In one embodiment of the foregoing methods, the cell is a neural cell. In another embodiment of the foregoing methods, The cell is in a subject.

In an embodiment of any of the foregoing methods, the compound has structure of Compound 100, Compound 100E, Compound 101, Compound 101E, Compound 102, Compound 102E, Compound 103, Compound 103E, Compound 104, Compound 104E, Compound 105, Compound 105E, Compound 106, Compound 106E, Compound 107, Compound 107E, Compound 108 or Compound 108E.

In an embodiment of any of the foregoing methods, the compound has the structure of Compound 201, Compound 203, Compound 204, Compound 205, Compound 206, Compound 207, Compound 207(*a*), Compound 208, Compound 209, Compound 210, Compound 211, Compound 212, Compound 213, or Compound 214.

Definitions

Certain embodiments of the disclosed compounds can contain a basic functional group, such as amino or alkylamino, and are thus capable of forming pharmaceutically acceptable salts with pharmaceutically acceptable acids, or contain an acidic functional group and are thus capable of forming pharmaceutically acceptable salts with bases. The instant compounds therefore may be in a salt form. As used herein, a "salt" is a salt of the instant compounds which has been modified by making acid or base salts of the compounds. The salt may be pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. For a description of possible salts, see, e.g., Berge et al. (1977) "Pharmaceutical Salts", *J. Pharm. Sci.* 66:1-19.

As used herein, "therapeutically effective amount" means an amount sufficient to treat a subject afflicted with a disease (e.g. a neurodegenerative disease) or to alleviate a symptom or a complication associated with the disease.

As used herein, a "neurodegenerative disease" refers to a disease in which degeneration occurs of either gray or white matter, or both, of the nervous system. Thus, such a disease can be diabetic neuropathy, senile dementias, Alzheimer's disease, Mild Cognitive Impairment (MCI), dementia, Lewy Body Dementia, Frontal Temporal Lobe dementia, Parkinson's Disease, facial nerve (Bell's) palsy, glaucoma, Huntington's chorea, amyotrophic lateral sclerosis (ALS), status epilepticus, non-arteritic optic neuropathy, intervertebral disc herniation, vitamin deficiency, prion diseases such as Creutzfeldt-Jakob disease, carpal tunnel syndrome, peripheral neuropathies associated with various diseases, including but not limited to, uremia, porphyria, hypoglycemia, Sjorgren Larsson syndrome, acute sensory neuropathy, chronic ataxic neuropathy, biliary cirrhosis, primary amyloidosis, obstructive lung diseases, acromegaly, malabsorption syndromes, polycythemia vera, IgA and IgG gammapathies, complications of various drugs (e.g., metronidazole) and toxins (e.g., alcohol or organophosphates), Charcot-Marie-Tooth disease, ataxia telangectasia, Friedreich's ataxia, amyloid polyneuropathies, adrenomyeloneuropathy, Giant axonal neuropathy, Refsum's disease, Fabry's disease and lipoproteinemia.

As used herein, "tauopathies" refers to a class of neurodegenerative diseases which result from aggregation of tau protein in neurofibrillary tangles. Examples of tauopathies include, but are not limited to, Alzheimer's disease, Frontotemproal dementia (Pick's disease), Progressive Supranuclear Palsy, and Corticobasal degeneration.

As used herein, "treating" means slowing, stopping or reversing the progression of a disease, particularly a neurodegenerative disease.

As used herein, "zwitterion" means a compound that is electrically neutral but carries formal positive and negative charges on different atoms. Zwitterions are polar, have high solubility in water have poor solubility in most organic solvents.

The compounds disclosed herein may also form zwitterions. For example, a compound having the structure

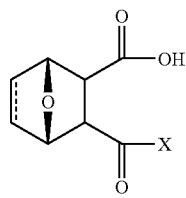

may also for the following zwitterionic structure

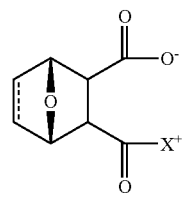

where X is as defined throughout the disclosures herein.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2, . . . , n-1 or n carbons in a linear or branched arrangement, and specifically includes methyl, ethyl, propyl, butyl, pentyl, hexyl, and so on. An embodiment can be $C_1$-$C_{12}$ alkyl. "Alkoxy" represents an alkyl group as described above attached through an oxygen bridge.

The term "alkenyl" refers to a non-aromatic hydrocarbon radical, straight or branched, containing at least 1 carbon to carbon double bond, and up to the maximum possible number of non-aromatic carbon-carbon double bonds may be present. Thus, $C_2$-$C_n$ alkenyl is defined to include groups having 1, 2, . . . , n-1 or n carbons. For example, "$C_2$-$C_6$ alkenyl", means an alkenyl radical having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be $C_2$-$C_{12}$ alkenyl.

The term "alkynyl", refers to a hydrocarbon radical straight or branched, containing at least 1 carbon to carbon triple bond, and up to the maximum possible number of non-aromatic carbon-carbon triple bonds may be present. Thus, $C_2$-$C_n$ alkynyl is defined to include groups having 1, 2, . . . , n-1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a $C_2$-$C_n$ alkynyl.

As used herein, "aryl" is intended to mean any stable monocyclic or bicyclic carbon ring of up to 10 atoms in each ring, wherein at least one ring is aromatic. Examples of such aryl elements include phenyl, naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring. The substituted aryls included in this invention include substitution at any suitable position with amines, substituted amines, alkylamines, hydroxys and alkylhydroxys, wherein the "alkyl" portion of the alkylamines and alkylhydroxys is a $C_2$-$C_n$ alkyl as defined hereinabove. The substituted amines may be substituted with alkyl, alkenyl, alkynl, or aryl groups as hereinabove defined.

The alkyl, alkenyl, alkynyl, and aryl substituents may be unsubstituted or unsubstituted, unless specifically defined otherwise. For example, a ($C_1$-$C_6$) alkyl may be substituted with one or more substituents selected from OH, oxo, halogen, alkoxy, dialkylamino, or heterocyclyl, such as morpholinyl, piperidinyl, and so on.

In the compounds of the present invention, alkyl, alkenyl, and alkynyl groups can be further substituted by replacing one or more hydrogen atoms by non-hydrogen groups described herein to the extent possible. These include, but are not limited to, halo, hydroxy, mercapto, amino, carboxy, cyano and carbamoyl. The term "substituted" as used herein means that a given structure has a substituent which can be an alkyl, alkenyl, or aryl group as defined above. The term shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

As used herein, "administering" an agent may be performed using any of the various methods or delivery systems well known to those skilled in the art. The administering can be performed, for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intrathecally, into a cerebral ventricle, intraventicularly, intratumorally, into cerebral parenchyma or intraparenchchymally.

The following delivery systems, which employ a number of routinely used pharmaceutical carriers, may be used but are only representative of the many possible systems envisioned for administering compositions in accordance with the invention.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's).

Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

It is understood that substituents and substitution patterns on the compounds of the instant invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

The compounds disclosed herein (Compounds 100-108, Compounds 100E to 108E, Compound 201, Compounds 203-214 and Compound 207(*a*)) were obtained from Lixte Biotechnology Holdings, Inc., 248 Route 25A, No. 2, East Setauket, N.Y.

Discussion

The compounds described herein are useful for the prevention and/or treatment of neurodegenerative conditions including Alzheimer's disease, Parkinson's disease, motor neuron diseases such as amyotrophic lateral sclerosis, and other neurodegenerative diseases collectively known as tauopathies.

Several of the compounds inhibit protein phosphatase 2A. These include Compounds 100, 102, 103, 104, 105, 106, 107, 108, 111, the structures of which are shown in Table 1. These compounds differ in substituents on portions of the core molecule Compound 100. These compounds show dose dependent inhibition of a broad spectrum of human cancer cell lines in vitro including SH-SY5Y, a dopaminergic neuronal line, frequently used as a model for assessing pharmacologic interventions relevant to human neuronal cells. Given intraperitoneally, these compounds enter the brain of the normal mouse as demonstrated by increased acetylation of histone 3 and 8.

The compounds increase the phosphorylation of several regulatory proteins including Akt. At low doses that are non-toxic to mice, these compounds slightly stimulate cell proliferation and increases phosphorylation of Akt in human cancer cell lines tested including SH-SY5Y. When given intraperitoneally to normal mice, Compound 100 and Compound 102 also increased Akt phosphorylation in the cell lines tested, growing as xenografts in SCID mice, as set forth in the examples herein.

Because the Compound-100 series of drugs increase cellular phosphorylated Akt at low non-toxic doses and also increase acetylation of histones in neurons of the intact animal, these compounds are useful for the treatment of neurodegenerative diseases, particularly Alzheimer's disease and all other tauopathies. While each of the compounds tested increase Akt phosphorylation of multiple tumor cell lines, they also increase Akt phosphorylation of the neuroblastoma cell line SH-SY5Y, a model of dopamine neurons.

The results with Compound 100 and Compound 102 show that each of these has properties that enhance their entry into the brain. Thus, these drugs are neuroprotective and useful for the prevention and/or treatment of neurodegereratve disease. The mechanism by which the Compound 100 series of compounds exert their neuroprotective effect may be by increasing the intra-neuronal cell activity of Akt-1 and enhancing the phosphorylation of GSK-3B. Each of these compounds when given by intraperitoneal injection, increase Akt phosphorylation in mouse neurons. This increase in Akt phosphorylation is associated with an increase in the phosphorylation of GSK-3β. Increased phosphorylation of GSK-3β is known to decrease its activity. Therefore, chronic suppression of GSK-3β activity by compound 100 homologs may reduce tau phosphorylation. Reduction in tau phosphorylation reduces the formation of paired helical filaments, an intervention that should lessen the progression of tauopathies including Alzheimer's disease, Parkinson's disease, amyotrophic lateral sclerosis, and other rarer neurodegenerative diseases characterized by abnormal depositions of tau molecules.

The compound 200 series, which include compounds 201, 207(*a*) and 203-214, the structures of which are shown in Table 2, are HDAC inhibitors.

TABLE 1

Compouns 100-108 and 111

Compound 100

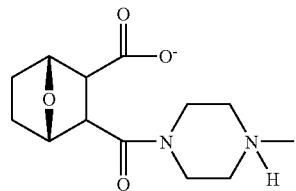

Compound 100E

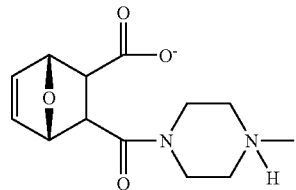

Compound 101

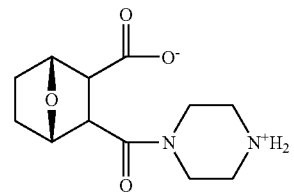

Compound 101E

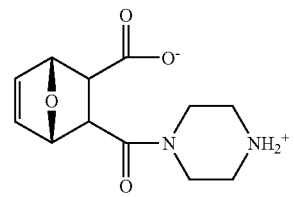

Compound 102

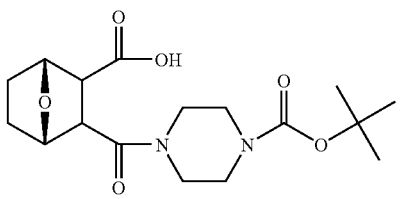

TABLE 1-continued
Compouns 100-108 and 111
Compound 102E
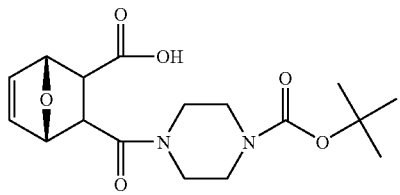
Compound 103
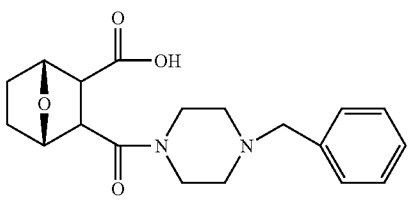
Compound 103E
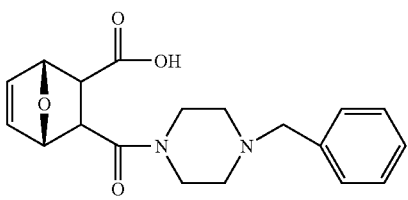
Compound 104
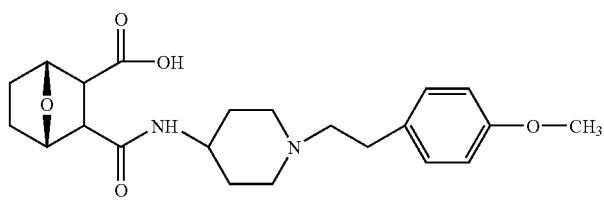
Compound 104E
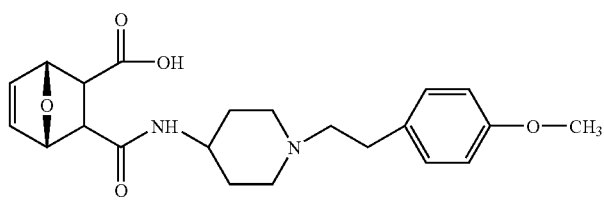
Compound 105
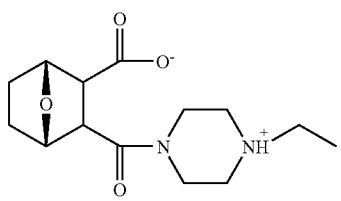
Compound 105E
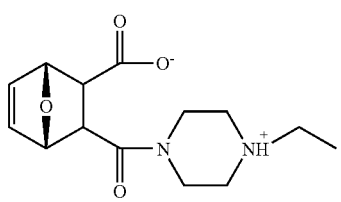

TABLE 1-continued
Compouns 100-108 and 111
Compound 106
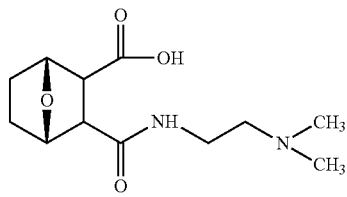
Compound 106E
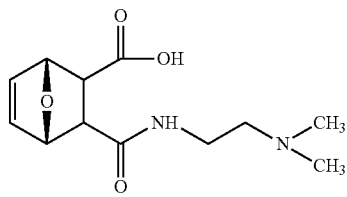
Compound 107
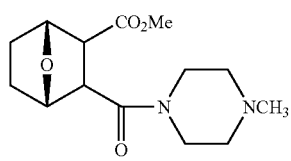
Compound 107E
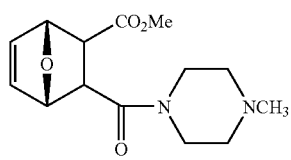
Compound 108
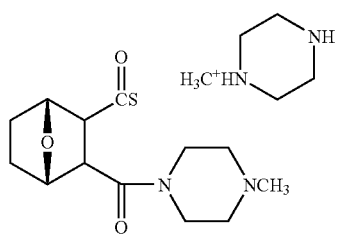
Compound 108E
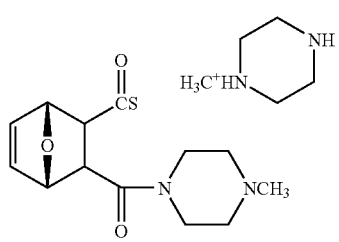
Compound 111
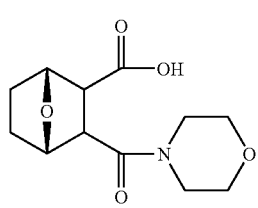

TABLE 2

| Compound | Structure |
|---|---|
| 201 | *N-phenyl-N'-(2-mercaptobenzoyl) pentanediamide structure* |
| 203 | *N,N'-bis(2-hydroxybenzoyl)hexane-1,6-diamine structure* |
| 204 | *N,N'-bis(2-mercaptobenzoyl)hexane-1,6-diamine structure* |
| 205 | *N-(pyridin-3-yl)-N'-(2-mercaptobenzoyl)pentanediamide structure* |
| 206 | *N-(4-dimethylaminophenyl)-N'-(2-mercaptobenzoyl)pentanediamide structure* |
| 207 | *nicotinamide-N(R$^{27}$)-butyl-NH-(5-chloro-2-mercaptobenzoyl) structure; wherein R$^{27}$ is H, alkyl, or aryl.* |
| 207a | *N-(pyridin-3-ylcarbonyl)-pentyl-NH-(5-chloro-2-mercaptobenzoyl) structure* |
| 208 | *N-(pyridin-3-ylcarbonyl)-pentyl-NH-(2-mercaptobenzoyl) structure* |

TABLE 2-continued

| Compound | Structure |
|---|---|
| 209 | (structure: 4-aminophenyl-NH-C(O)-(CH2)4-NH-C(O)-2-mercaptophenyl) |
| 210 | (structure: phenyl-NH-C(O)-(CH2)4-NH-C(O)-2-mercapto-5-chlorophenyl) |
| 211 | (structure: phenyl-NH-C(O)-(CH2)4-NH-C(O)-2-mercapto-5-methoxyphenyl) |
| 212 | (structure: phenyl-NH-C(O)-(CH2)5-NH-C(O)-2-mercaptophenyl) |
| 213 | (structure: phenyl-NH-C(O)-(CH2)6-NH-C(O)-2-mercaptophenyl) |
| 214 | (structure: phenyl-NH-C(O)-(CH2)8-NH-C(O)-2-mercaptophenyl) |

EXPERIMENTAL DETAILS

First Series of Experiments

In Vivo Experiments

Human medulloblastoma DAOY cells were implanted subcutaneously in SCID mice. Mice were then treated with 0.03 mg/20 gram mouse with Compound 100 or vehicle alone. After 4 hours and 24 hours, western blots were made for phosphorylated Akt (p-Akt), total Akt, and beta actin. Control cells at both time points had only trace amount of p-Akt and substantial amounts of total Akt and beta actin. Exposure to compound 100 revealed induction of p-Akt and an increase in total Akt relative to beta actin, as shown in FIG. 3.

Human glioblastoma U87 cells were implanted subcutaneously in SCID mice. Mice were then treated with 0.03 mg/20 gram mouse with Compound 100 or vehicle alone. After 4 hours, western blots were made for p-Akt, total Akt, and beta actin. Control cells showed only trace amounts of p-Akt and substantial amounts of total Akt and beta actin. Exposure to Compound 100 revealed induction of p-Akt and an increase in total Akt relative to beta actin, as shown in FIG. 5.

Normal mice were treated with Compound 100 or Compound 102 at a dose of 0.03 mg/20 gram mouse, or with vehicle. After 4 hours of exposure, treated and control animals were sacrificed and western blots for acetylated histone 3 and histone 4 were made. As showing in FIG. 6, both drugs increased acetylation of the histones compared to control tissue.

In Vitro Experiments:

Medulloblastoma cells, DAOY, were grown in culture and exposed to Compound 100, Compound X or vehicle alone. After 4 hours western blots were made for p-Akt, total Akt and beta actin. Control cells showed only trace amounts of p-Akt and substantial amounts of total Akt and beta actin. Exposure to the control agent Compound 205, an investigational histone deacetylase inhibitor, had little effect. Exposure to Compound 100 revealed induction of p-Akt and an increase in total Akt relative to beta actin.

Human glioblastoma cells, U87, were grown in culture and exposed to Compound 100 or vehicle alone. After 4 hours, western blots were made for p-Akt, total Akt, and beta actin. Control cells showed only trace amounts of p-Akt and substantial amounts of total Akt and beta actin. Exposure to Compound 100 revealed induction of p-Akt and an increase in total akt relative to beta actin, as shown in FIG. 4.

Neuroprotective and neurotrophic effects of a novel HDAC inhibitor, compound 201, and a novel protein phosphatase 2A inhibitor, compound 102, on primary rat cortical neurons.

The effects of two novel compounds, compound 201, a class I and II HDAC inhibitor (HDACi), and compound 102, a protein phosphatase 2A inihibitor (PP2Ai), on neuronal cell characteristics including physiological responses to signalling agents, differentiation and maturation in culture, and survival following environmental stress were investigated. Neurite extension was evaluated after Calcein staining using commercially available software. Exposure to either compound 201 or compound 102 at 250 and 500 nM resulted in increased total neurite outgrowth and increased process length and then was evaluated for their ability to sustain neuron integrity over time after exposure to stress.

Neurons were chronically or acutely treated with each compound and exposed to environmental stress (replacement of the culture medium with a saline PBS based solution for one hour followed by removal of the PBS medium and restoration of standard neuronal culture medium) and then observed for survival (FIG. 6). Compound 201 displayed marked neurotrophic effects as evidenced by maintenance for up to 21 days neuronal cell numbers. In contrast, cells exposed to either DMSO (the vehicle used for the compounds) or just saline showed a 3.5 fold reduction in cell numbers (FIG. 7). Compound 102 had little effect on cell number. To assess the effects of compound 102 and compound 201, independently, on neuronal function, the ability of the neurons in a culture dish to respond to exposure to glutamate was studied. In vitro, neurons respond to glutamate with the activation of several receptors associated with different transducing mechanisms. The assortment of glutamate sensitive receptors in a given neuronal population depends on maturation and differentiation. After seven days in culture, there is an assortment of glutamate receptors, including the AMPA/Kainate and NMDA receptors. AMPA/Kainate receptors are in general maximally expressed in the first few days in vitro followed by a gradual decline, while NMDA receptor expression increases over time, reaching a maximum after 7 days in vitro. AMPA/Kainate responses to exposure to glutamate as measured by calcium flux are characterized by fast desensitization (i.e. very little measurable calcium increase), while NMDA responses are characterized by an elevation of calcium concentration that persists as long as glutamate is applied. In the absence of test drug, there was variability in glutamate responsiveness dependent on NMDA receptor expression. A typical response of neurons in culture to glutamate characteristic of the NMDA receptors consists of a rapid increase and a high plateau phase of calcium (FIGS. 8-10). Repeat experiments showed variability in the extent of this response indicating that the time-point in culture is a moment at which NMDA receptor expression is variable. Exposures to 500 nM compound 201 (FIGS. 11-14) and, independently, to 500 nM compound 102 (FIGS. 15-18) for 24 h prior exposure to glutamate, however, were associated with a statistically significant increase in the NMDA type response to glutamate ($p \leq 0.001$), particularly in neurons showing the smallest response to glutamate (FIGS. 11-14). This modulation is compatible with a positive neurotrophic effect of compound 201. A similar smaller but statistically significant effect ($p \leq 0.01$) was associated with compound 102 (FIG. 19).

REFERENCES

1. Burke, R. E., *Pharmacology and Therapeutics* (2007) 114: 262-277.
2. Schapira, A. H. V. and Olanow, C. W., *JAMA* (2004) 291: 358-364
3. Ries, V. et al., *PNAS* (2006) 103:18757-18762
4. Sontag, E et al., *Neuron* (1996) 17:1201-1207
5. Tian, Q. and Wang, J., *Neurosignals* (2002) 11:262-269
6. Gong et al 2005 *J Neural Transm.* (2005) 112(6):813-38
7. Meske, V. et al., *The Journal of Biological Chemistry*, (2008) 283:100-109.
8. Grimes and Jope, *Progress In Neurobiology* (2001) 65:391-426
9. Liu, F. et al., *Journal of Neurochemistry* (2005) 95:1363-1372
10. Kaytor, M. D. and Orr, H. T. *Current Opinion in Neurobiology* (2002) 12:275-278
11. Baki, L. et al, *The Journal of Neuroscience* (2008)
12. Shen, J. et al., *Cell* (1997) 89:629-639
13. Wong, P. C. et al., *Adv. Exp. Med. Biol.* (1998) 446:145-159
14. Sherrington, R. et al., *Nature* (1995) 375:754-760
15. Baki, L. et al., *The EMBO Journal* (2004) 23:2586-2596
16. Kang, D. E. et al., *The Journal of Biological Chemistry* (2005) 280:31537-31547
17. Uemura, K. et al., *The Journal of Biological Chemistry* (2007) 282:15823-18832
18. Engel, T. et al., *The Journal of Neurosciences* (2006) 26:5083-5090
19. Korzus, E. et al., *Neuron* (2004) 42:961-972
20. Levenson, J. M. et al., *The Journal of Biological Chemistry* (2004) 279:40545-40559
21. Beglopoulos, V. and Shen, J., *TRENDS in Pharmacological Sciences* (2006) 27:33-40
22. Fischer, A. et al., *Nature* (2007) 447:178-182; doi:1038/nature05772
23. Sweat, J. D. et al., *Nature* (2007) 447:151-152
24. Mangan, K. P. and Levenson, J. M., *Cell* (2007) 129:851-853
25. Albert, M. S., *New Engl. J. Med.* (2007) 357(5):502-503
26. Abel, T and Zukin, R. S., *Current Opinion in Pharmacology* (2008) 8:57-64

What is claimed is:

1. A method for reducing the amount of active GSK-3B or increasing the amount of phosphorylated Akt in a neural cell comprising contacting the cell with an effective amount of a compound having the structure

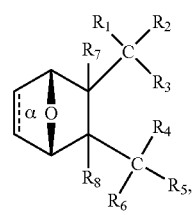

wherein
bond α is present or absent;
$R_1$ and $R_2$ is each independently H, O⁻ or $OR_9$,
where $R_9$ is H, alkyl, alkenyl, alkynyl or aryl, or $R_1$ and $R_2$ together are =O;
$R_3$ and $R_4$ are each different, and each is OH, O⁻, OR$_9$, SH, S⁻, SR$_9$,

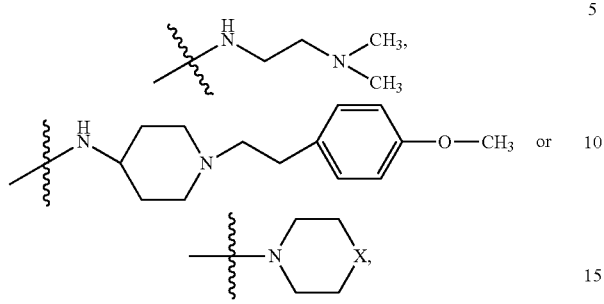

where X is O, S, NR$_{10}$, or N⁺R$_{10}$R$_{10}$,
  where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O,

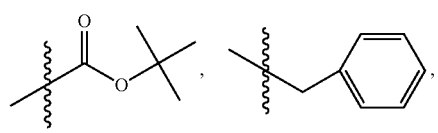

—CH$_2$CN, —CH$_2$CO$_2$R$_{11}$, —CH$_2$COR$_{11}$, —NHR$_{11}$ or —NH⁺(R$_{11}$)$_2$,
  where each $R_{11}$ is independently alkyl, alkenyl or alkynyl, each of which is substituted or unsubstituted, or H;
$R_5$ and $R_6$ is each independently H, OH, or $R_5$ and $R_6$ taken together are =O; and
$R_7$ and $R_8$ is each independently H, F, Cl, Br, SO$_2$Ph, CO$_2$CH$_3$, or SR$_{12}$,
  where $R_{12}$ is H, aryl or a substituted or unsubstituted alkyl, alkenyl or alkynyl, or a salt, enantiomer or zwitterion of the compound
so as to thereby reduce the amount of GSK-3B or increase the amount of phosphorylated Akt in the neural cell.

2. The method of claim 1, wherein $R_4$ is

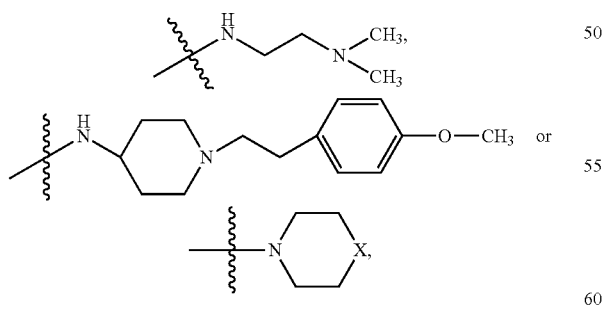

where X is O, NR$_{10}$, N⁺R$_{10}$R$_{10}$
  where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O,

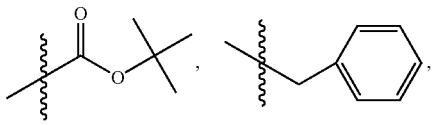

—CH$_2$CN, —CH$_2$CO$_2$R$_{11}$, —CH$_2$COR$_{11}$, —NHR$_{11}$ or —NH⁺(R$_{11}$)$_2$,
  where $R_{11}$ is H or alkyl.

3. The method of claim 1, wherein bond α is present.

4. The method of claim 1, wherein bond α is absent.

5. The method of claim 1, wherein the compound has the structure

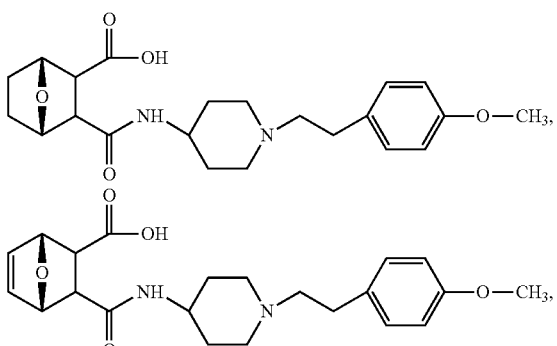

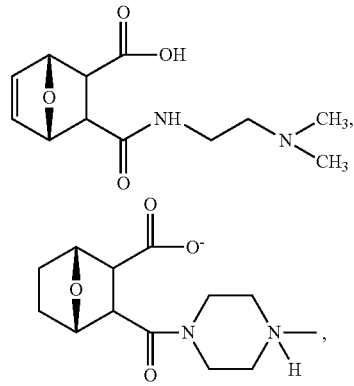

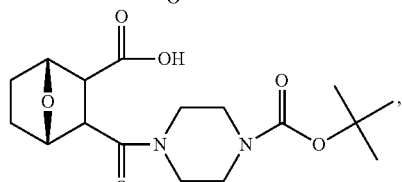

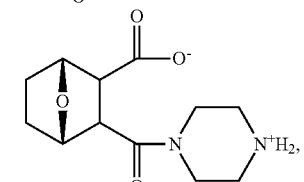

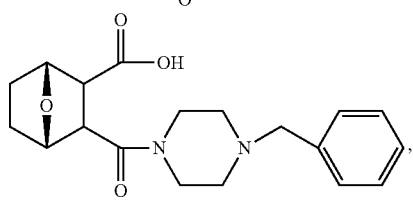

-continued
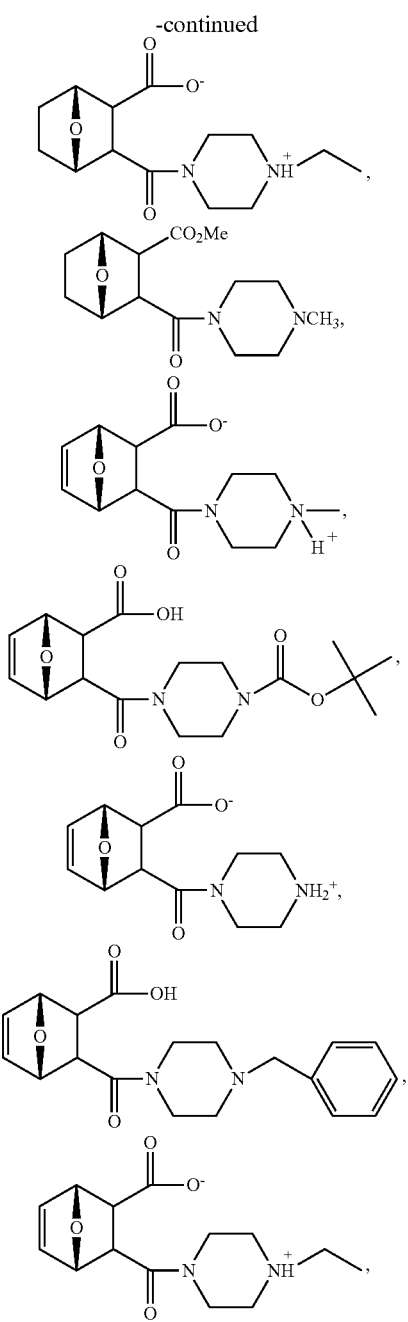
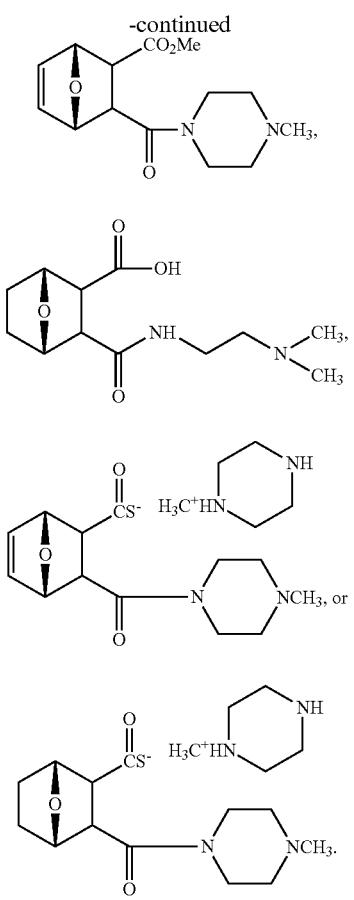
6. The method of claim 5, wherein the compound has the structure
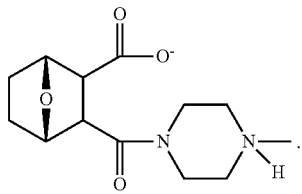
* * * * *